United States Patent
Treco et al.

(10) Patent No.: US 6,565,844 B1
(45) Date of Patent: *May 20, 2003

(54) PROTEIN PRODUCTION AND PROTEIN DELIVERY

(75) Inventors: Douglas Treco, Arlington, MA (US); Michael W. Heartlein, Boxborough, MA (US); Richard F Selden, Wellesley, MA (US)

(73) Assignee: Transkaryotic Therapies, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/312,245

(22) Filed: May 14, 1999

Related U.S. Application Data

(63) Continuation of application No. 08/451,894, filed on May 26, 1995, now Pat. No. 5,968,502, which is a division of application No. 07/985,586, filed on Dec. 3, 1992, now abandoned, and a continuation-in-part of application No. 07/911,533, filed on Jul. 10, 1992, now abandoned, which is a continuation-in-part of application No. 07/789,188, filed on Nov. 5, 1991, now abandoned, and a continuation-in-part of application No. 07/787,840, filed on Nov. 5, 1991, now abandoned.

(51) Int. Cl.$^7$ ............................................. A61K 48/00
(52) U.S. Cl. ................... 424/93.21; 424/93.2; 514/44; 435/69.1; 435/91.4; 435/320.1; 435/325; 435/455
(58) Field of Search ............................ 424/93.2, 93.21, 424/429, 465; 514/44; 435/320.1, 455, 69.1, 325; 536/23.1, 24.1

(56) References Cited

U.S. PATENT DOCUMENTS

| | | | |
|---|---|---|---|
| 4,497,796 A | 2/1985 | Salser | 424/95 |
| 4,703,008 A | 10/1987 | Lin | 435/325 |
| 4,751,348 A | 6/1988 | Malmberg et al. | 800/1 |
| 4,789,550 A | 12/1988 | Hommel et al. | 424/493 |
| 4,892,538 A | 1/1990 | Aebisher et al. | 604/891.1 |
| 5,171,674 A | 12/1992 | Stevens et al. | 435/69.1 |
| 5,272,071 A | 12/1993 | Chappel | 435/455 |
| 5,312,912 A * | 5/1994 | Hadwiger et al. | 536/24.1 |
| 5,356,804 A | 10/1994 | Desnick et al. | 435/208 |
| 5,547,933 A | 8/1996 | Lin | 514/8 |
| 5,578,461 A | 11/1996 | Sherwin et al. | 435/69.1 |
| 5,618,698 A | 4/1997 | Lin | 435/69.4 |
| 5,621,080 A | 4/1997 | Lin | 530/350 |
| 5,631,153 A * | 5/1997 | Capecchi et al. | 435/455 |
| 5,641,670 A * | 6/1997 | Treco et al. | 435/320.1 |
| 5,652,340 A * | 7/1997 | Kohwi-Shigematsu et al. | 530/358 |
| 5,733,761 A * | 3/1998 | Treco et al. | 435/455 |
| 5,736,359 A * | 4/1998 | Grisvekd et al. | 435/69.1 |
| 5,756,349 A | 5/1998 | Lin | 435/325 |
| 5,789,215 A | 8/1998 | Berns et al. | 435/455 |
| 5,955,422 A | 9/1999 | Lin | 514/8 |
| 5,968,502 A * | 10/1999 | Treco et al. | 424/93.21 |

FOREIGN PATENT DOCUMENTS

| | | |
|---|---|---|
| EP | 0 038 765 B | 9/1987 |
| EP | 0 452 894 A | 10/1991 |
| EP | 0 529 300 A1 | 7/1992 |
| EP | 0 289 034 | 11/1996 |
| GB | 2 159 172 | 11/1985 |
| WO | WO 87/00201 | 11/1987 |
| WO | WO 88/08306 | 11/1988 |
| WO | WO 89/01517 | 2/1989 |
| WO | WO 90/06757 | 6/1990 |
| WO | WO/11354 | 10/1990 |
| WO | WO 91/06666 | 5/1991 |
| WO | WO 91/06667 | 5/1991 |
| WO | WO 91/09955 | 7/1991 |
| WO | WO 91/13151 | 9/1991 |
| WO | WO 91/19796 | 12/1991 |
| WO | WO 93/03164 | 2/1993 |
| WO | WO 93/09222 | 5/1993 |
| WO | WO 94/05784 | 3/1994 |
| WO | WO 94/10567 | 5/1994 |
| WO | WO 94/12650 | 7/1994 |
| WO | WO 95/18858 | 7/1995 |
| WO | WO 95/21626 | 8/1995 |
| WO | WO 95/31560 | 8/1995 |

OTHER PUBLICATIONS

Marshall, Science, vol. 269, pp. 1050–1055, 1995.*
Crystal, Science, vol. 270, pp. 404–410, 1995.*
Coghlan, News Scientist, vol. 149, p. 14 and 15, 1995.*
Capecchi, "Altering the Genome By Homologous Recombination," Science, 244:1288–1292, (Jun. 1989).
Capecchi, "Researchers Can Now Create Mice Bearing Any Chosen Mutations In Any Known Gene. The Technology Is Revolutionizing the Study of Mammalian Biology," Scientific American, pp. 52–59, (Mar. 1994).
Capecchi, "The New Mouse Genetics: Altering the Genome By Gene Targeting," Trends in Genetics, 5(3):70–76, (Mar. 1989).
Darnell et al., "DNA Synthesis, Repair, and Recombination," Molecular Cell Biology, (Scientific American Books distributed by W. H. Freeman and Co., New York, NY), eds.:555–565 (1986).
Folger et al., "Patterns of Integration of DNA Microinjected Into Cultured Mammalian Cells: Evidence for Homologous Recombination Between Injected Plasmid DNA Molecules," Molecular and Cellular Biology, 2(11):1372–1387, (Nov. 1982).

(List continued on next page.)

Primary Examiner—Dave T. Nguyen
(74) Attorney, Agent, or Firm—Fish & Richardson P.C.

(57) ABSTRACT

The present invention relates to DNA constructs that alter the expression of a targeted gene in a cell when the DNA construct is homologously recombined with a target site within the chromosomal DNA of the cell, as well as to a cell into which has been incorporated a new transcription unit containing an exogenous regulatory sequence operatively linked to an endogenous gene of the cell's chromosomal DNA. These constructs and cells can be used in a method of altering expression of the targeted gene.

11 Claims, 5 Drawing Sheets

OTHER PUBLICATIONS

Griffiths et al., "Mechanisms of Genetic Change II: Recombination," An Introduction to Genetic Analysis, 6$^{th}$ ed. (W.H. Freeman and Co., New York, NY), Chapter 20:617–636, (1996).
Joyner et al., "Retrovirus Long Terminal Repeats Activate Expression of Coding Sequences for the Herpes Simplex Virus Thymidine Kinase Gene," Proc. Natl. Acad. Sci. USA, 79:1573–1577 (1982).
Kaetzel et al., "Expression of Biologically Active Bovine Luteinizing Hormone In Chinese Hamster Ovary Cells," Proc. Natl. Acad. Sci. USA, 82:7280–7283, (Nov. 1985).
Lin et al., "Cloning and Expression of the Human Erythropoietin Gene," Proc. Natl. Acad. Sci. USA, 82:7580–7584, (Nov. 1985).
Powell et al., "Human Erythropoietin Gene: High Level Expression in Stably Transfected Mammalian Cells and Chromosome Localization," Proc. Natl. Acad. Sci. USA, 83:6465–6469, (Sep. 1986).
Rubnitz et al., "The Minimum Amount of Homology Required for Homologous Recombination in Mammalian Cells" Molecular and Cellular Biol., 4:2253–2258 (1984).
Smithies et al., "Insertion of DNA Sequences Into the Human Chromosomal β–Globin Locus By Homologous Recombination," Nature, 317:230–234, (1985).
Yanagi et al., "Recombinant Human Erythropoietin Produced by Namalwa Cells," DNA, 8(6):419–427, (1989).
Alberts, Molecular Biology of the Cell (Glossary), third edition, Garland Publishing, Inc., New York.
Antin et al., Biotechniques, 6:640–42 (1988).
ATCC Catalogue of Cell Lines & Hybridomas, pp. 1–5, 42, 67, 85, 139, 147 (1985).
ATCC Catalogue of Fungi/Yeasts, pp. 324–346 (1987).
Bartley et al., Cell, 77:1117–1124 (1994).
Behr et al., Proc. Nat'l Acad. Sci. USA, 86:6982–86 (1989).
Bennett et al., Mol. Biol. Med., 7:471–77 (1990).
Boggs, S., International Journal of Cell Cloning, 8:80–96 (1990).
Brash et al., Mol. Cell. Biol., 7:2031–34 (1987).
Brenner et al., Mol. Biol. Med., 7:105–15 (1990).
Brigham et al., Am. J. Respir. Cell. Mol. Biol., 1:95–100 (1989).
Browne et al., Cold Spring Harbor Symposia on Quantitative Biology, vol. L1, Cold Spring Harbor Laboratory, p. 693–702 (1986).
Burrin et al., Mol. Endocrinol., 3:1643–51 (1989).
Busby et al., Nature, 316:217–273 (1985).
Cann et al., Oncogen, 3:123–28 (1988).
Capecchi, Science, 244:1288–1292 (1989).
Chang et al., Biochem. Biophys. Act., 1092:153–160 (1991).
Chang et al., Mol. Biol. Med., 7:461–70 (1990).
Claverlie et al., Nature, 371:752 (1994).
Cline, Pharmac. Ther., 29:69–92 (1986).
Daubas et al., Nucleic Acids Research, 16(4):1251–1271 (1988).
De la Salle et al., Nature, 316:268–270 (1985).
de Sauvage et al., Nature, 369:533–538 (1994).
Diatloff–Zito et al., Proc. Nat'l Acad. Sci. USA, 83:7034–38 (1986).
Doering et al., J. Neurosci. Res., 29:292–98 (1991).
Doetschmann et al., PNAS, 85:8583–8587 (1988).
Drucker et al., J. Biol. Chem., 261:9637–9653 (1986).
Duncan & Reddell, Biochemistry (Moscow), 621263–1274 (1997).
Editorial from Nature Biotechnology, 15:815 (1997).
Faulds et al., Drugs, 38:863–899 (1989).
Foster et al., Proc. Natl. Acad. Sci. USA, 91:13023–13027 (1994).
Fountain et al., Gene, 68:167–172 (1988).
French Anderson, Nature, 392 (Supp):25–30 (1998).
Friedmann, Science, 244:1275–1280 (1989).
Fuchs et al., New Eng. J. Med., 331:367–642 (1994).
Gao et al., Biochem. Biophys. Res. Commun., 179:280–85 (1991).
Gareis et al., Cell. Mol. Biol., 37:191–203 (1991).
Ginot et al., Eur. J. Biochem., 180:289–94 (1989).
Glover (ed.), IRL Press, pp. 144–148 (1985).
Harper et al., J. Invest. Dermatol., 91:150–53 (1988).
Hesse et al., Proc. Nat'l Acad. Sci USA, 83:4312–16 (1986).
Iannuzzi et al., Am. Rev. Respir. Dis., 138:965–68 (1988).
Itzhaki et al., Nucleic Acids Research, 19(14):3835–42 (1991).
Jensen et al., Exp. Cell Res., 189:163–68 (1990).
Jurka et al., J. Mol. Evol., 32:105–121 (1991).
Kaufman, Technique, 2:221–236 (Oct. 1990).
Kaushansky et al., Nature, 369:568–571 (1994).
Keating et al., Exp. Hematol., 18:99–102 (1990).
Keating et al., Prog. Clin. Biol. Res., 333:491–98 (1990).
Keene et al., The Journal of Biochemistry, 264:4769–4775 (1989).
Kremer et al., J. Clin. Invest., 87:884–93 (1991).
LeMouellic et al., PNAS, 87:4712–16 (1990).
Li et al., Cancer Research, 50:5328–5332 (Sep. 1, 1990).
Litwer et al., J. Biol. Chem., 264:14597–600 (1988).
Loeffler et al., J. Neurochem., 54:1812–15 (1990).
Lok et al., Nature, 369:565–568 (1994).
Lu et al., Pfugers Arch., 415:198–203 (1989).
Mansour et al., Nature, 336:348–352 (1988).
May and Sehgal, J. of Interferon Research, 5:521–526 (1985).
McDonald, Experimental Hematology, 16:201–205 (1988) (in Chemical Abstracts 108:124584).
Mercola et al., Ann. NY Acad. Sci., 397:272–80 (1982).
Mes–Masson et al., J. Cell. Sci., 94:517–25 (1989).
Metcalf, Nature, 369:519–520 (1994).
Migliaccio et al., The Journal of Cell Biology, 109:833–841 (1989).
Morgan et al., Science, 237:1476–1479 (1987).
Nagy et al., Journal of Cell Science, 87:651–655 (1987).
Narayanan et al., Biochem. Biophys. Res. Commun., 141:1018–24 (1986).
Ohno et al., Nucleic Acids Research, 10:967–977 (1982).
Orkin et al., Report and Recommendations of the Panel to Assess the NIH Investment in Research on Gene Therapy, NIH, 1995.
Palmiter et al., Science, 222:809–814 (1983).
Pasco et al., DNA, 8:535–41 (1989).
Pecceu et al., Gene, 97:253–258 (1991).
Pentchev et al., The Journal of Biological Chemistry, 218:5256–5261 (1973).
Ponder et al., Hum. Gene. Ther., 2:41–52 (1991).
Ponticelli et al., Nephron, 52:201–208 (1989).
Potter, Anal. Biochem., 174:361–73 (1988).
Rippe et al., Mol. Cell. Biol., 10:689–95 (1990).
Robertson, Biol. Reprod., 44:238–45 (1991).
Scharfmann et al., Proc. Nat'l. Acad. Sci. USA, 88:4626–30 (1991).

Sedivy et al., Proc. Nat'l. Acad. Sci. USA, 86:227–231 (1989).
Selden et al., Science, 236:714–18 (1987).
Selden et al., New England Journal of Medicine, 317(17):1067–76 (1987).
Shak et al., PNAS, 87:9188–9192 (Dec. 1990).
Shesely et al., Proc. Nat'l. Acad. Sci. USA, 88:4294–98 (1991).
Sohma et al., FEBS Lett., 353:57–61 (1994).
Sorge et al., PNAS, 84:906–909 (1987).
Stacey et al., Immunol. Cell. Biol., 71 (Pt 2):75–85 (1993).
Tatsuka et al., Exp. Cell Res., 178:154–62 (1988).
Thomas et al., Nature, 346:847–50 (1990).
Thomas et al., Cell, 51:503–512 (1987).
Thompson et al., Cell, 56:313–21 (1989).
Toneguzzo et al., Proc. Nat'l Acad. Sci., 83:3496–99 (1986).
Tur–kaspa et al., Mol. Cell. Biol., 6:716 (1986).
Vega, Hum. Genet., 87:245–53 (1991).
Verma, Scientific American, 68–84 (11/90).
Verma et al., Nature, 389:239–242 (1997).
Vogelstein et al., Trends Genet 9, 138–141 (1993).
Weidle et al., Gene, 73:427–37 (1988).
Werner et al., J. Neurosci. Res., 25:50–57 (1990).
Wolff et al., Science, 247:1465–1468 (1990).
Yang et al., Proc. Nat'l Acad. Sci. USA, 87:9568–72 (1990).
Zheng et al., Proc. Nat'l Acad. Sci. USA, 88:8067–71 (1991).

* cited by examiner

SEQUENCE LISTING (1) GENERAL INFORMATION:

(iii) NUMBER OF SEQUENCES: 17

(2) INFORMATION FOR SEQ ID NO: 1:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 1:

AGCTTCTGGG CTTCCAGAC                              19

(2) INFORMATION FOR SEQ ID NO: 2:

(i) SEQUENCE CHARACTERISTICS:
         (A) LENGTH: 16 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 2:

GGGGTCCCTC AGCGAC                                 16

(2) INFORMATION FOR SEQ ID NO: 3:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 3:

TGGGCTTCCA GACCCAG                                17

(2) INFORMATION FOR SEQ ID NO: 4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

```
CCAGCTACTT TGCGGAACTC                                             20
```

(2) INFORMATION FOR SEQ ID NO: 5:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

```
AAAAGTCGAC GGTACCTTGG TTTTTAAAAC CAGCCTGGAG                        40
```

(2) INFORMATION FOR SEQ ID NO: 6:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

```
CCTAGCGGCA ATGGCTACAG GTGAGTACTC GCGGGCTGGG CG                     42
```

(2) INFORMATION FOR SEQ ID NO: 7:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

```
CGCCCAGCCC GCGAGTACTC ACCTGTAGCC ATTGCCGCTA GG                     42
```

(2) INFORMATION FOR SEQ ID NO: 8:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 8:

```
TTTTCTCGAG CTAGAACAGA TAGCCAGGCT GAGAG                             35
```

(2) INFORMATION FOR SEQ ID NO: 9:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

```
CCTAGCGGCA ATGGCTACAG GTGAGTACTC AAGCTTCTGG GCTTCCAGAC CCAG          54
```

(2) INFORMATION FOR SEQ ID NO: 10:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

```
CTGGGTCTGG AAGCCCAGAA GCTTGAGTAC TCACCTGTAG CCATTGCCGC TAGG          54
```

(2) INFORMATION FOR SEQ ID NO: 11:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

```
TTTTCTCGAG CTCCGCGCCT GGCCGGGGTC CCTC          34
```

(2) INFORMATION FOR SEQ ID NO: 12:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 12:

```
AAAAAGATCT GGTACCTTGG TTTTTAAAAC CAGCCTGGAG          40
```

(2) INFORMATION FOR SEQ ID NO: 13:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 13:

```
TTTTGTCGAC GGTACCTTGG TTTTTAAAAC C          31
```

(2) INFORMATION FOR SEQ ID NO: 14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 14:

CACCTAAAAT GATCTCTCTG G                                      21

(2) INFORMATION FOR SEQ ID NO: 15:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

CGCGCCGGGT GACCACACCG GGGGCCCTAG ATCTGGTGAA GCTGGAGCTA CGGAGTAA      58

(2) INFORMATION FOR SEQ ID NO: 16:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 16:

TTACTCCGTA GCTCCAGCTT CACCAGATCT AGGGCCCCCG GTGTGGTCAC CCGGCGCG      58

(2) INFORMATION FOR SEQ ID NO: 17:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

GTCTCACCGT GATATTCTCG G                                      21

PROTEIN PRODUCTION AND PROTEIN DELIVERY

RELATED APPLICATION

This application is a continuation of application Ser. No. 08/451,894, filed May 26, 1995, issued as U.S. Pat. No. 5,968,502, which is a divisional of application Ser. No. 07/985,586, filed Dec. 3, 1992, abandoned, which is a Continuation-In-Part of application Ser. No. 07/789,188, filed on Nov. 5, 1991, abandoned, and is also a Continuation-In-Part of application Ser. No. 07/911,533, filed on Jul. 10, 1992, abandoned, and is also a Continuation-In-Part of application Ser. No. 07/787,840, filed on Nov. 5, 1991, abandoned, all of which are incorporated herein by reference.

BACKGROUND OF THE INVENTION

Current approaches to treating disease by administering therapeutic proteins include in vitro production of therapeutic proteins for conventional pharmaceutical delivery (e.g. intravenous, subcutaneous, or intramuscular injection) and, more recently, gene therapy.

Proteins of therapeutic interest are generally produced by introducing exogenous DNA encoding the protein of therapeutic interest into appropriate cells. Presently-available approaches to gene therapy make use of infectious vectors, such as retroviral vectors, which include the genetic material to be expressed. Such approaches have limitations, such as the potential of generating replication-competent virus during vector production; recombination between the therapeutic virus and endogenous retroviral genomes, potentially generating infectious agents with novel cell specificities, host ranges, or increased virulence and cytotoxicity; independent integration into large numbers of cells, increasing the risk of a tumorigenic insertional event; limited cloning capacity in the retrovirus (which restricts therapeutic applicability) and short-lived in vivo expression of the product of interest. A better approach to providing gene products, particularly one which avoids the risks associated with presently available methods and provides long-term treatment, would be valuable.

SUMMARY OF THE INVENTION

The present invention relates to improved methods for both the in vitro production of therapeutic proteins and for the production and delivery of therapeutic proteins by gene therapy. The present method describes an approach which activates expression of endogenous cellular genes, and further allows amplification of the activated endogenous cellular genes, which does not require in vitro manipulation and transfection of exogenous DNA encoding proteins of therapeutic interest.

The present invention relates to transfected cells, both transfected primary or secondary cells (i.e., non-immortalized cells) and transfected immortalized cells, useful for producing proteins, particularly therapeutic proteins, methods of making such cells, methods of using the cells for in vitro protein production and methods of gene therapy. Cells of the present invention are of vertebrate origin, particularly of mammalian origin and even more particularly of human origin. Cells produced by the method of the present invention contain exogenous DNA which encodes a therapeutic product, exogenous DNA which is itself a therapeutic product and/or exogenous DNA which causes the transfected cells to express a gene at a higher level or with a pattern of regulation or induction that is different than occurs in the corresponding nontransfected cell.

The present invention also relates to methods by which primary, secondary, and immortalized cells are transfected to include exogenous genetic material, methods of producing clonal cell strains or heterogenous cell strains, and methods of immunizing animals, or producing antibodies in immunized animals, using the transfected primary, secondary, or immortalized cells.

The present invention relates particularly to a method of gene targeting or homologous recombination in cells of vertebrate, particularly mammalian, origin. That is, it relates to a method of introducing DNA into primary, secondary, or immortalized cells of vertebrate origin through homologous recombination, such that the DNA is introduced into genomic DNA of the primary, secondary, or immortalized cells at a preselected site. The targeting sequences used are determined by (selected with reference to) the site into which the exogenous DNA is to be inserted. The present invention further relates to homologously recombinant primary, secondary, or immortalized cells, referred to as homologously recombinant (HR) primary, secondary or immortalized cells, produced by the present method and to uses of the HR primary, secondary, or immortalized cells.

The present invention also relates to a method of activating (i.e., turning on) a gene present in primary, secondary, or immortalized cells of vertebrate origin, which is normally not expressed in the cells or is not expressed at physiologically significant levels in the cells as obtained. According to the present method, homologous recombination is used to replace or disable the regulatory region normally associated with the gene in cells as obtained with a regulatory sequence which causes the gene to be expressed at levels higher than evident in the corresponding nontransfected cell, or to display a pattern of regulation or induction that is different than evident in the corresponding nontransfected cell. The present invention, therefore, relates to a method of making proteins by turning on or activating an endogenous gene which encodes the desired product in transfected primary, secondary, or immortalized cells.

In one embodiment, the activated gene can be further amplified by the inclusion of a selectable marker gene which has the property that cells containing amplified copies of the selectable marker gene can be selected for by culturing the cells in the presence of the appropriate selectable agent. The activated endogenous gene which is near or linked to the amplified selectable marker gene will also be amplified in cells containing the amplified selectable marker gene. Cells containing many copies of the activated endogenous gene are useful for in vitro protein production and gene therapy.

Gene targeting and amplification as disclosed in the present invention are particularly useful for turning on the expression of genes which form transcription units which are sufficiently large that they are difficult to isolate and express, or for turning on genes for which the entire protein coding region is unavailable or has not been cloned. The present invention also describes a method by which homologous recombination is used to convert a gene into a cDNA copy, devoid of introns, for transfer into yeast or bacteria for in vitro protein production.

Transfected cells of the present invention are useful in a number of applications in humans and animals. In one embodiment, the cells can be implanted into a human or an animal for protein delivery in the human or animal. For example, human growth hormone (hGH), human EPO (hEPO), human insulinotropin and other proteins can be delivered systemically or locally in humans for therapeutic benefits. Barrier devices, which contain transfected cells which express a therapeutic product and through which the therapeutic product is freely permeable, can be used to retain cells in a fixed position in vivo or to protect and isolate the cells from the host's immune system. Barrier devices are particularly useful and allow transfected immortalized cells, transfected cells from another species (transfected xenogeneic cells), or cells from a nonhistocompatibility-matched donor (transfected allogeneic cells) to be implanted for treatment of human or animal conditions or for agricultural uses (e.g., meat and dairy production). Barrier devices also allow convenient short-term (i.e., transient) therapy by providing ready access to the cells for removal when the treatment regimen is to be halted for any reason. Transfected xenogeneic and allogeneic cells may be used for short-term gene therapy, such that the gene product produced by the cells will be delivered in vivo until the cells are rejected by the host's immune system.

Transfected cells of the present invention are also useful for eliciting antibody production or for immunizing humans and animals against pathogenic agents. Implanted transfected cells can be used to deliver immunizing antigens that result in stimulation of the host's cellular and humoral immune responses. These immune responses can be designed for protection of the host from future infectious agents (i.e., for vaccination), to stimulate and augment the disease-fighting capabilities directed against an ongoing infection, or to produce antibodies directed against the antigen produced in vivo by the transfected cells that can be useful for therapeutic or diagnostic purposes. Removable barrier devices can be used to allow a simple means of terminating exposure to the antigen. Alternatively, the use of cells that will ultimately be rejected (xenogeneic or allogeneic transfected cells) can be used to limit exposure to the antigen, since antigen production will cease when the cells have been rejected.

The methods of the present invention can be used to produce primary, secondary, or immortalized cells producing a wide variety of therapeutically useful products, including (but not limited to): hormones, cytokines, antigens, antibodies, enzymes, clotting factors, transport proteins, receptors, regulatory proteins, structural proteins, transcription factors, or anti-sense RNA. Additionally, the methods of the present invention can be used to produce cells which produce non-naturally occurring ribozymes, proteins, or nucleic acids which are useful for in vitro production of a therapeutic product or for gene therapy.

DETAILED DESCRIPTION OF THE INVENTION

Overview of the Invention

Figure 1:
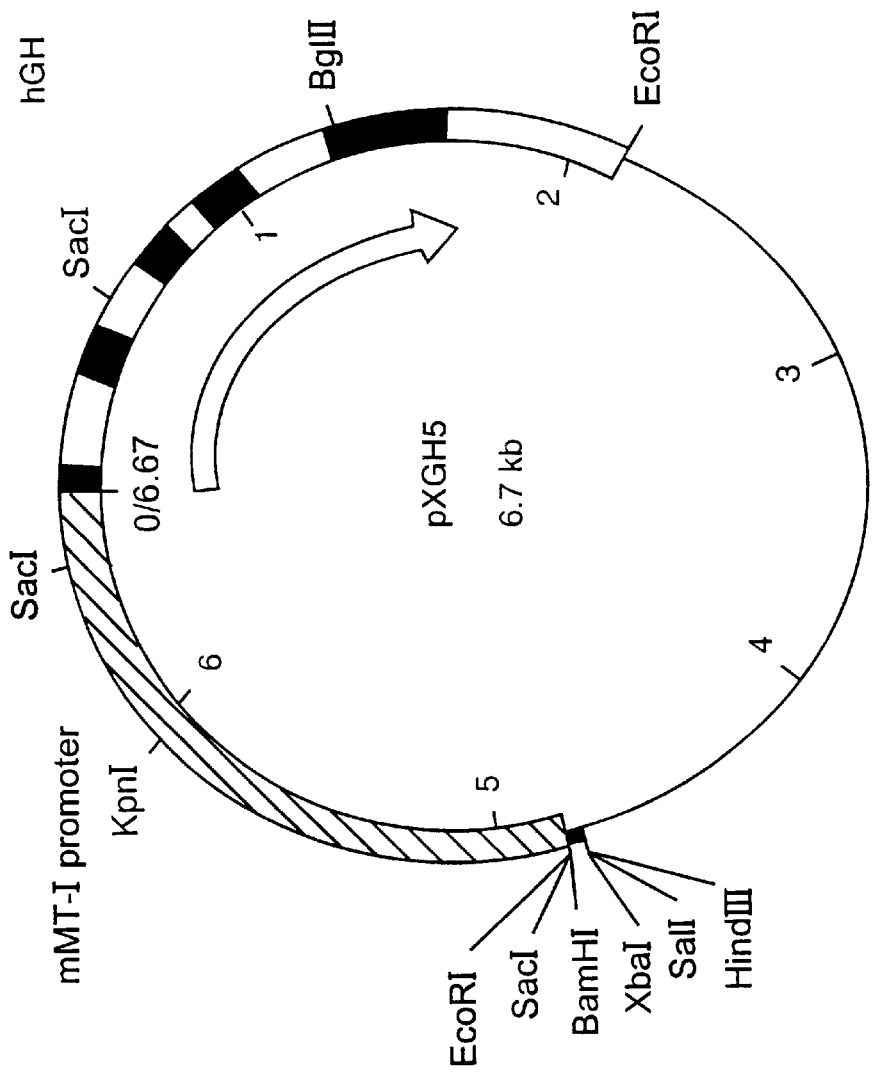
FIG. 1 is a schematic representation of plasmid pXGH5, which includes the human growth hormone (hGH) gene under the control of the mouse metallothionein promoter.

The present invention and the methods described in the applications incorporated herein by reference relate to transfected primary, secondary, and immortalized cells of vertebrate origin, particularly mammalian origin, transfected with exogenous genetic material (DNA or RNA) which encodes a clinically useful product, methods by which primary, secondary, and immortalized cells are transfected to include exogenous genetic material, methods of producing clonal cell strains or heterogenous cell strains which express exogenous genetic material, a method of providing clinically useful products in physiologically useful quantities to an individual in need thereof through the use of transfected cells of the present invention, methods of vaccinating animals for protection against pathogenic viruses or microbial agents expressing epitopes antigenically related to products expressed by the transfected cells and methods of producing antibodies directed against a product made by the transfected primary, secondary, or immortalized cells. Clinically useful products can be produced in vitro, by purification from the transfected cells, or produced in vivo, by implantation into a non-human animal or human (i.e., gene therapy). Whether produced in vitro or in vivo, the clinically useful products can include hormones, cytokines, antigens, antibodies, enzymes, clotting factors, transport proteins, receptors, regulatory proteins, structural proteins, transcription factors, anti-sense RNA. Additionally, the methods of the present invention can be used to produce cells which produce non-naturally occurring ribozymes, proteins, or nucleic acids.

In one embodiment, the present invention relates to a method of gene or DNA targeting in cells of vertebrate, particularly mammalian, origin. That is, it relates to a method of introducing DNA into primary, secondary, or immortalized cells of vertebrate origin through homologous recombination or targeting of the DNA, which is introduced into genomic DNA of the primary, secondary, or immortalized cells at a preselected site. The targeting sequences used are determined by (selected with reference to) the site into which the exogenous DNA is to be inserted. The present invention further relates to homologously recombinant primary, secondary or immortalized cells, referred to as homologously recombinant (HR) primary, secondary or immortalized cells, produced by the present method and to uses of the HR primary, secondary, or immortalized cells.

The present invention also relates to a method of activating a gene which is present in primary cells, secondary cells or immortalized cells of vertebrate origin, but is normally not expressed in the cells or is not expressed at significant levels in the cells. Homologous recombination or targeting is used to replace or disable the regulatory region normally associated with the gene with a regulatory sequence which causes the gene to be expressed at levels higher than evident in the corresponding nontransfected cell, or causes the gene to display a pattern of regulation or induction that is different than evident in the corresponding nontransfected cell. The present invention, therefore, relates to a method of making proteins by activating an endogenous gene which encodes the desired product in transfected primary, secondary or immortalized cells.

Several embodiments in which exogenous DNA undergoes homologous recombination with genomic DNA of transfected (recipient) cells can be practiced according to the present invention. In one embodiment, introduction of the exogenous DNA results in the activation of a gene that is normally not expressed or expressed in levels too low to be useful for in vitro protein production or gene therapy. In a second embodiment, sequences encoding a product of therapeutic utility are directed to integrate into the recipient cell genome via homologous recombination at a preselected site in the recipient cell's genome, such that the site of integration is precisely known and the site can be chosen for its favorable properties (e.g., the site allows for high levels of expression of exogenous DNA).

In a third embodiment, the present invention describes a method of activating (i.e. turning on) and amplifying an endogenous gene encoding a desired product in a transfected, primary, secondary, or immortalized cell. That is, it relates to a method of introducing, by homologous recombination with genomic DNA, DNA sequences which are not normally functionally linked to the endogenous gene and (1) which, when inserted into the host genome at or near the endogenous gene, serve to alter (e.g., activate) the expression of the endogenous gene, and further (2) allow for selection of cells in which the activated endogenous gene is amplified. Amplifiable DNA sequences useful in the present invention include, but are not limited to, sequences which encode the selectable markers dihydrofolate reductase, adenosine deaminase, and the CAD gene (encoding the trifunctional protein carbamyl phosphate synthase, aspartate transcarbamylase, and dihydro-orotase). Improved versions of these sequences and other amplifiable sequences can also be used. According to the present method, the amplifiable DNA sequences encoding a selectable marker and the DNA sequences which alter the regulation of expression of the endogenous gene are introduced into the primary, secondary, or immortalized cell in association with DNA sequences homologous to genomic DNA sequences at a preselected site in the cell's genome. This site will generally be within or upstream of a gene encoding a therapeutic product or at a site that affects the desired gene's function. The DNA sequences which alter the expression of the endogenous gene, the amplifiable sequences which encode a selectable marker, and the sequences which are homologous to a preselected site in genomic DNA can be introduced into the primary, secondary, or immortalized cell as a single DNA construct, or as separate DNA sequences which become physically linked in the genome of a transfected cell. Further, the DNA can be introduced as linear, double stranded DNA, with or without single stranded regions at one or both ends, or the DNA can be introduced as circular DNA. After the exogenous DNA is introduced into the cell, the cell is maintained under conditions appropriate for homologous recombination to occur between the genomic DNA and a portion of the introduced DNA. Homologous recombination between the genomic DNA and the introduced DNA results in a homologously recombinant primary, secondary, or immortalized cell in which sequences which alter the expression of an endogenous gene, and the amplifiable sequences encoding a selectable marker, are operatively linked to an endogenous gene encoding a therapeutic product. Culturing the resulting homologously recombinant cell under conditions which select for amplification of the amplifiable DNA encoding a selectable marker results in a cell containing an amplified selectable marker and a coamplified endogenous gene whose expression has been altered. Cells produced by this method can be cultured under conditions suitable for the expression of the therapeutic protein, thereby producing the therapeutic protein in vitro, or the cells can be used for in vivo delivery of a therapeutic protein (i.e., gene therapy).

Additional embodiments are possible. The targeting event can be a simple insertion of a regulatory sequence, placing the endogenous gene under the control of the new regulatory sequence (for example, by insertion of either a promoter or an enhancer, or both, upstream of an endogenous gene). The targeting event can be a simple deletion of a regulatory element, such as the deletion of a tissue-specific negative regulatory element. The targeting event can replace an existing element; for example, a tissue-specific enhancer can be replaced by an enhancer that has broader or different cell-type specificity than the naturally-occurring elements, or displays a pattern of regulation or induction that is different from the corresponding nontransfected cell. In this embodiment the naturally occurring sequences are deleted and new sequences are added. In all cases, the identification of the targeting event can be facilitated by the use of one or more selectable marker genes that are physically associated with the targeting DNA, allowing for the selection of cells in which the exogenous DNA has integrated into the host cell genome. The identification of the targeting event can also be facilitated by the use of one or more marker genes exhibiting the property of negative selection, such that the negatively selectable marker is linked to the exogenous DNA, but configured such that the negatively selectable marker flanks the targeting sequence, and such that a correct homologous recombination event with sequences in the host cell genome does not result in the stable integration of the negatively selectable marker. Markers useful for this purpose include the Herpes Simplex Virus thymidine kinase (TK) gene or the bacterial xanthine-guanine phosphoribosyl-transferase (gpt) gene.

The present invention also relates to a method by which homologous recombination is used to convert a gene into a cDNA copy (a gene copy devoid of introns). The cDNA copy can be transferred into yeast or bacteria for in vitro protein production, or the cDNA copy can be inserted into a mammalian cell for protein production. If the cDNA is to be transferred to microbial cells, two DNA constructs containing targeting sequences are introduced by homologous recombination, one construct upstream of and one construct downstream of a human gene encoding a therapeutic protein. The sequences introduced upstream include DNA sequences homologous to genomic DNA sequences at or upstream of the DNA encoding the first amino acid of a mature, processed therapeutic protein; a retroviral LTR; sequences encoding a marker for selection in microbial cells; a regulatory element that functions in microbial cells; and DNA encoding a leader peptide that promotes secretion from microbial cells. The sequences introduced upstream are introduced near to and upstream of genomic DNA encoding the first amino acid of a mature, processed therapeutic protein. The sequences introduced downstream include DNA sequences homologous to genomic DNA sequences at or downstream of the DNA encoding the last amino acid of a mature, processed protein; a microbial transcriptional termination sequence; sequences capable of directing DNA replication in microbial cells; and a retroviral LTR. The sequences introduced downstream are introduced adjacent to and downstream of the DNA encoding the stop codon of the mature, processed therapeutic protein. After introducing into the cells each of the two DNA constructs, the cells are maintained under conditions appropriate for homologous recombination between the introduced DNA and genomic DNA, thereby producing homologously recombinant cells. Optionally, one or both of the DNA constructs can encode one or more markers for either positive or negative selection of cells containing the DNA construct, and a selection step can be added to the method after one or both of the DNA constructs have been introduced into the cells. Alternatively, the sequences encoding the marker for selection in microbial cells and the sequences capable of directing DNA replication in microbial cells can both be present in either the upstream or the downstream targeting construct, or the marker for selection in microbial cells can be present in the downstream targeting construct and the sequences capable of directing DNA replication in microbial cells can be present in the upstream targeting construct. The homologously recombinant cells are then cultured under conditions appropriate for LTR directed transcription, processing and reverse transcription of the RNA product of the gene encoding the therapeutic protein. The product of reverse transcription is a DNA construct comprising an intronless DNA copy encoding the therapeutic protein, operatively linked to DNA sequences comprising the two exogenous DNA constructs described above. The intronless DNA construct produced by the present method is then introduced into a microbial cell. The microbial cell is then cultured under conditions appropriate for expression and secretion of the therapeutic protein.

Transfected Cells

As used herein, the term primary cell includes cells present in a suspension of cells isolated from a vertebrate tissue source (prior to their being plated, i.e., attached to a tissue culture substrate such as a dish or flask), cells present in an explant derived from tissue, both of the previous types of cells plated for the first time, and cell suspensions derived from these plated cells. The term secondary cell or cell strain refers to cells at all subsequent steps in culturing. That is, the first time a plated primary cell is removed from the culture substrate and replated (passaged), it is referred to herein as a secondary cell, as are all cells in subsequent passages. Secondary cells are cell strains which consist of secondary cells which have been passaged one or more times. A cell strain consists of secondary cells that: 1) have been passaged one or more times; 2) exhibit a finite number of mean population doublings in culture; 3) exhibit the properties of contact-inhibited, anchorage dependent growth (anchorage-dependence does not apply to cells that are propagated in suspension culture); and 4) are not immortalized.

Cells transfected by the subject method fall into four types or categories: 1) cells which do not, as obtained, make or contain the therapeutic product, 2) cells which make or contain the therapeutic product but in smaller quantities than normal (in quantities less than the physiologically normal lower level) or in defective form, 3) cells which make the therapeutic product at physiologically normal levels, but are to be augmented or enhanced in their content or production, and 4) cells in which it is desirable to change the pattern of regulation or induction of a gene encoding a therapeutic product.

Primary and secondary cells to be transfected by the present method can be obtained from a variety of tissues and include all cell types which can be maintained in culture. For example, primary and secondary cells which can be transfected by the present method include fibroblasts, keratinocytes, epithelial cells (e.g., mammary epithelial cells, intestinal epithelial cells), endothelial cells, glial cells, neural cells, formed elements of the blood (e.g., lymphocytes, bone marrow cells), muscle cells and precursors of these somatic cell types. Primary cells are preferably obtained from the individual to whom the transfected primary or secondary cells are administered. However, primary cells can be obtained from a donor (other than the recipient) of the same species or another species (e.g., mouse, rat, rabbit, cat, dog, pig, cow, bird, sheep, goat, horse).

Transfected primary and secondary cells have been produced, with or without phenotypic selection, as described in the copending U.S. patent applications Ser. Nos. 07/787,840 and 07/911,533 and shown to express exogenous DNA encoding a therapeutic product including, for example, hGH, EPO and insulinotropin.

Immortalized cells can also be transfected by the present method and used for either protein production or gene therapy. Examples of immortalized human cell lines useful for protein production or gene therapy by the present method include, but are not limited to, HT1080, HeLa, MCF-7 breast cancer cells, K-562 leukemia cells, KB carcinoma cells and 2780AD ovarian carcinoma cells. Immortalized cells from other species (e.g., chinese hamster ovary (CHO) cells or mouse L cells) can be used for in vitro protein production or gene therapy. In addition, primary or secondary human cells, as well as primary or secondary cells from other species which display the properties of gene amplification in vitro can be used for in vitro protein production or gene therapy.

Exogenous DNA

Exogenous DNA incorporated into primary, secondary or immortalized cells by the present method is: 1) DNA which encodes a translation or transcription product whose expression in cells is desired, or a portion of a translation or transcription product, such as a protein product or RNA product useful to treat an existing condition or prevent it from occurring (eg., hGH, EPO or insulino-tropin); or 2) DNA which does not encode a gene product but is itself useful, such as a transcriptional regulatory sequence or DNA useful to treat an existing condition or prevent it from occurring.

DNA transfected into primary, secondary or immortalized cells can encode an entire desired product, or can encode, for example, the active or functional portion(s) of the product.

The product can be, for example, a hormone, a cytokine, an antigen, an antibody, an enzyme, a clotting factor, a transport protein, a receptor, a regulatory protein, a structural protein, a transcription factor, an anti-sense RNA, or a ribozyme. Additionally, the product can be a protein or a nucleic acid which does not occur in nature (i.e., a novel protein or novel nucleic acid). The DNA can be obtained from a source in which it occurs in nature or can be produced, using genetic engineering techniques or synthetic processes. The DNA can encode one or more therapeutic products. After transfection, the exogenous DNA is stably incorporated into the recipient cell's genome (along with any additional sequences present in the DNA construct used), from which it is expressed or otherwise functions. Alternatively, the exogenous DNA can be used to target to DNA that exists episomally within cells.

DNA encoding the desired product can be introduced into cells under the control of an inducible promoter, with the result that cells as produced or as introduced into an individual do not express the product but can be induced to do so (i.e., production is induced after the transfected cells are produced but before implantation or after implantation). DNA encoding the desired product can, of course, be introduced into cells in such a manner that it is expressed upon introduction (i.e., without induction).

As taught herein, gene targeting can be used to replace a gene's existing regulatory region with a regulatory sequence isolated from a different gene or a novel regulatory sequence synthesized by genetic engineering methods. Such regulatory sequences can be comprised of promoters, enhancers, scaffold-attachment regions, negative regulatory elements, transcriptional initiation sites, regulatory protein binding sites or combinations of said sequences. (Alternatively, sequences which affect the structure or stability of the RNA or protein produced can be replaced, removed, added, or otherwise modified by targeting, these sequences including polyadenylation signals, mRNA stability elements, splice sites, leader sequences for enhancing or modifying transport or secretion properties of the protein, or other sequences which alter or improve the function or stability of protein or RNA molecules). According to this method, introduction of the exogenous DNA results in disablement of the endogenous sequences which control expression of the endogenous gene, either by replacing all or a portion of the endogenous (genomic) sequence or otherwise disrupting the function of the endogenous sequence. In the situation where targeting is used to replace a protein coding domain, chimeric, multifunctional proteins can be produced which combine structural, enzymatic, or ligand or receptor binding properties from two or more proteins into one polypeptide.

Selectable Markers

A variety of selectable markers can be incorporated into primary, secondary or immortalized cells. For example, a selectable marker which confers a selectable phenotype such as drug resistance, nutritional auxotrophy, resistance to a cytotoxic agent or expression of a surface protein, can be used. Selectable marker genes which can be used include neo, gpt, dhfr, ada, pac, hyg, CAD, and hisD. The selectable phenotype conferred makes it possible to identify and isolate recipient cells. Amplifiable genes encoding selectable markers (e.g., ada, dhfr and the multifunctional CAD gene which encodes carbamyl phosphate synthase, aspartate transcarbamylase, and dihydro-orotase) have the added characteristic that they enable the selection of cells containing amplified copies of the selectable marker inserted into the genome. This feature provides a mechanism for significantly increasing the copy number of an adjacent or linked gene for which amplification is desirable.

Selectable markers can be divided into two categories: positively selectable and negatively selectable (in other words, markers for either positive selection or negative selection). In positive selection, cells expressing the positively selectable marker are capable of surviving treatment with a selective agent (such as neo, gpt, dhfr, ada, pac, hyg, mdrl and hisD). In negative selection, cells expressing the negatively selectable marker are destroyed in the presence of the selective agent (e.g., tk, gpt).

DNA Constructs

DNA constructs, which include exogenous DNA and, optionally, DNA encoding a selectable marker, along with additional sequences necessary for expression of the exogenous DNA in recipient cells, are used to transfect primary, secondary or immortalized cells in which the encoded product is to be produced. The DNA construct can also include targeting sequences for homologous recombination with host cell DNA. DNA constructs which include exogenous DNA sequences which do not encode a gene product (and are the therapeutic product) and, optionally, include DNA encoding a selectable marker, can be used to transfect primary, secondary or immortalized cells. The DNA constructs may be introduced into cells by a variety of methods, including electroporation, microinjection, calcium phosphate precipitation, and liposome- polybrene- or DEAE dextran-mediated transfection. Alternatively, infectious vectors, such as retroviral, herpes, adenovirus, adenovirus-associated, mumps and poliovirus vectors, can be used to introduce the DNA.

In one embodiment, the DNA construct includes exogenous DNA and one or more targeting sequences, generally located at both ends of the exogenous DNA sequence. Targeting sequences are DNA sequences normally present in the genome of the cells as obtained (e.g., an essential gene, a nonessential gene or noncoding DNA, or sequences present in the genome through a previous modification). Such a construct is useful to integrate exogenous DNA (at a preselected cite in a recipient cell is genome) encoding a therapeutic product, such as a hormone, a cytokine, an antigen, an antibody, an enzyme, a clotting factor, a transport protein, a receptor, a regulatory protein, a structural protein, an anti-sense RNA, a ribozyme or a protein or a nucleic acid which does not occur in nature. In particular, exogenous DNA can encode one of the following: Factor VIII, Factor IX, erythropoietin, alpha-1 antitrypsin, calcitonin, glucocerebrosidase, growth hormone, low density lipoprotein (LDL) receptor, apolipoproteins (e.g. apolipoprotein E or apolipoprotein A-I), IL-2 receptor and its antagonists, insulin, globin, immunoglobulins, catalytic antibodies, the interleukins, insulin-like growth factors, superoxide dismutase, immune responder modifiers, parathyroid hormone, interferons, nerve growth factors, tissue plasminogen activators, and colony stimulating factors, and variants of these proteins which have improved or novel biological properties or more desirable half-life or turnover times in vivo Such a construct is also useful to integrate exogenous DNA (at a preselected site in a recipient cell's genome) which is a therapeutic product, such as DNA sequences sufficient for sequestration of a protein or nucleic acid in the transfected primary or secondary cell, DNA sequences which bind to a cellular regulatory protein, DNA sequences which alter the secondary or tertiary chromosomal structure and DNA sequences which are transcriptional regulatory elements into genomic DNA of primary or secondary cells.

The exogenous DNA, targeting sequences and selectable marker can be introduced into cells on a single DNA construct or on separate constructs. The total length of the DNA construct will vary according to the number of components (exogenous DNA, targeting sequences, selectable marker gene) and the length of each. The entire construct length will generally be at least 20 nucleotides. In a construct in which the exogenous DNA has sufficient homology with genomic DNA to undergo homologous recombination, the construct will include a single component, the exogenous DNA. In this embodiment, the exogenous DNA, because of its homology, serves also to target integration into genomic DNA and additional targeting sequences are unnecessary. Such a construct is useful to knock out, replace or repair a resident DNA sequence, such as an entire gene, a gene portion, a regulatory element or portion thereof or regions of DNA which, when removed, place regulatory and structural sequences in functional proximity. It is also useful when the exogenous DNA contains a marker useful for selection or amplification of linked sequences.

In a second embodiment, the DNA construct includes exogenous DNA, targeting DNA sequences and DNA encoding at least one selectable marker. In this second embodiment, the order of construct components can be: targeting sequences-exogenous DNA-DNA encoding a selectable marker(s)-targeting sequences. In this embodiment, one or more selectable markers are included in the construct, which makes selection based on a selectable phenotype possible. Cells that stably integrate the construct will survive treatment with the selective agent; a subset of the stably transfected cells will be HR cells, which can be identified by a variety of techniques, including PCR, Southern hybridization and phenotypic screening.

In a third embodiment, the order of components in the DNA construct can be: targeting sequence—selectable marker 1—targeting sequence—selectable marker 2. In this embodiment selectable marker 2 displays the property of negative selection. That is, the gene product of selectable marker 2 can be selected against by growth in an appropriate media formulation containing an agent (typically a drug or metabolite analog) which kills cells expressing selectable marker 2. Recombination between the targeting sequences flanking selectable marker 1 with homologous sequences in the host cell genome results in the targeted integration of selectable marker 1, while selectable marker 2 is not integrated. Such recombination events generate cells which are stably transfected with selectable marker 1 but not stably transfected with selectable marker 2, and such cells can be selected for by growth in the media containing the selective agent which selects for selectable marker 1 and the selective agent which selects against selectable marker 2.

Figure 2:
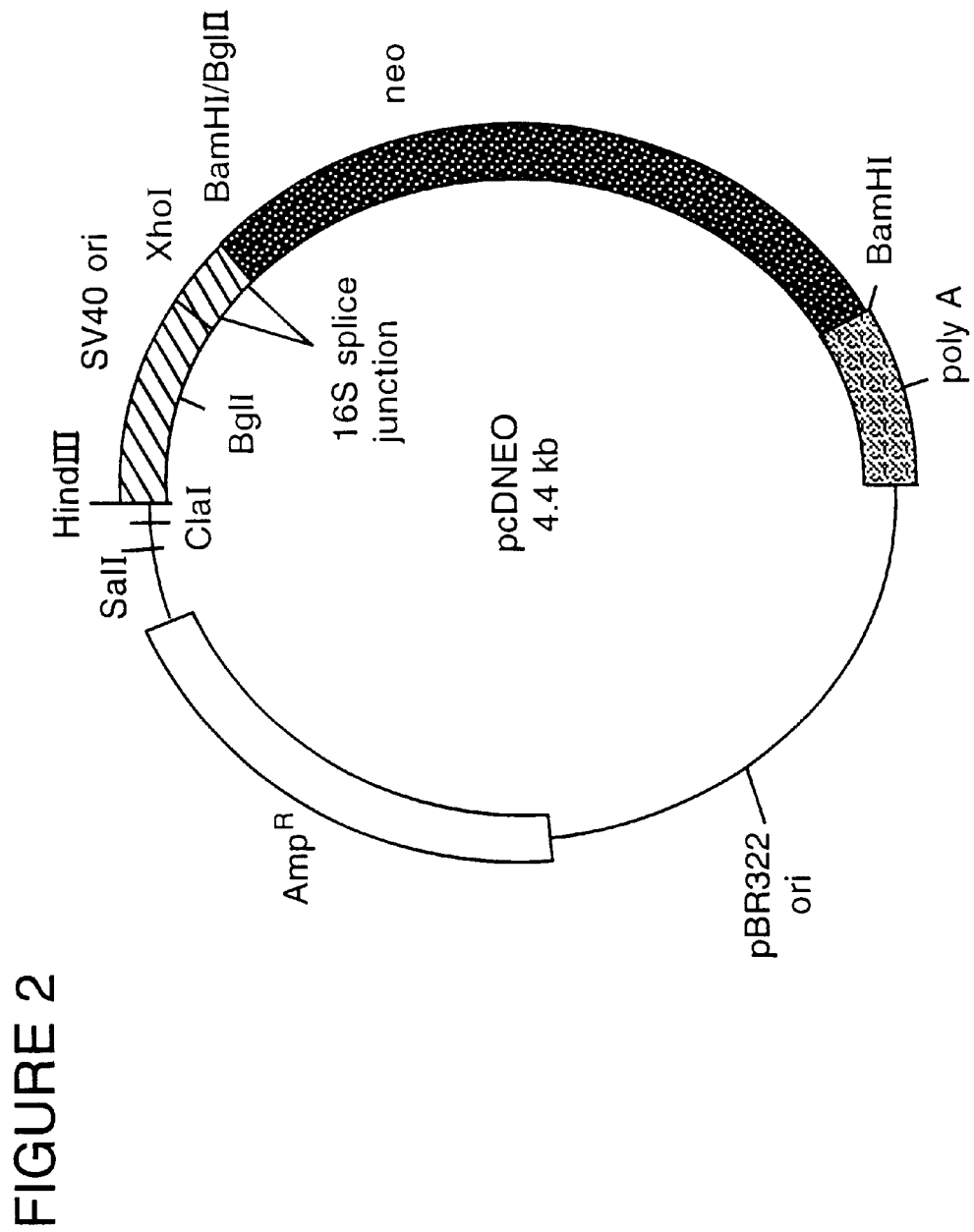
FIG. 2 is a schematic representation of plasmid pcDNEO, which includes the neo coding region (BamHI-BglII fragment) from plasmid pSV2neo inserted into the BamHI site of plasmid pcD; the Amp-R and pBR3220ri sequences from pBR322; and the polyA, 16S splice junctions and early promoter regions from SV40.

A DNA construct can include an inducible promoter which controls expression of the exogenous DNA, making inducible expression possible. optionally, the DNA construct can include a bacterial origin of replication and bacterial antibiotic resistance markers, which allow for large-scale plasmid propagation in bacteria. A DNA construct which includes DNA encoding a selectable marker, along with additional sequences, such as a promoter, polyadenylation site and splice junctions, can be used to confer a selectable phenotype upon transfected primary or secondary cells (e.g., plasmid pcDNEO, schematically represented in FIG. 2). Such a DNA construct can be co-transfected into primary or secondary cells, along with a targeting DNA sequence, using methods described herein.

In all embodiments of the DNA construct, exogenous DNA can encode one or more products, can be one or more therapeutic products or one or more of each, thus making it possible to deliver multiple products.

Uses of Transfected Cells

Cells produced using the methods and DNA constructs described herein can be used for a wide variety of purposes. Primary, secondary, or immortalized cells of vertebrate origin can be produced in which 1) DNA already present in a recipient cell is repaired, altered, deleted, or replaced; 2) a gene or DNA sequence which encodes a therapeutic product (or other desired product) or is itself a therapeutic product is introduced into the genome of a recipient cell at a preselected site (i.e. gene targeting); 3) regulatory sequences present in the primary, secondary or immortalized cell recipients have been repaired, altered, deleted or replaced; or 4) an entire gene or gene portion has been repaired, altered, deleted, or replaced. Homologous recombination can also be used to produce universal donor cells, in which cell surface markers involved in histocompatibility have been altered, deleted or replaced, or in which the expression of such markers is altered, impaired, or eliminated.

The cells of the present invention are useful for in vitro production of therapeutic products which can be purified and delivered by conventional pharmaceutic routes. For example, primary, secondary, or immortalized human cells can be transfected with exogenous DNA containing a regulatory region which, upon homologous recombination with genomic DNA sequences, results in the replacement of an endogenous target gene's regulatory region with a regulatory region that allows novel expression and/or regulation of the target gene and, ultimately, production of a therapeutically useful product by the transfected cell. The activated endogenous target gene can further be amplified if an appropriate selectable marker gene is included in the targeting DNA. With or without amplification, these cells can be subject to large-scale cultivation for harvest of intracellular or extracellular protein products.

Transfected cells of the present invention are useful, as populations of transfected primary cells, transfected clonal cell strains, transfected heterogenous cell strains, and as cell mixtures in which at least one representative cell of one of the three preceding categories of transfected cells is present, as a delivery system for treating an individual with an abnormal or undesirable condition which responds to delivery of a therapeutic product, which is either: 1) a therapeutic protein (e.g., a protein which is absent, underproduced relative to the individual's physiologic needs, defective or inefficiently or inappropriately utilized in the individual; a protein with novel functions, such as enzymatic or transport functions) or 2) a therapeutic nucleic acid (e.g., DNA which binds to or sequesters a regulatory protein, RNA which inhibits gene expression or has intrinsic enzymatic activity). In the method of the present invention of providing a therapeutic protein or nucleic acid, transfected primary cells, clonal cell strains or heterogenous cell strains are administered to an individual in whom the abnormal or undesirable condition is to be treated or prevented, in sufficient quantity and by an appropriate route, to express or make available the exogenous DNA at physiologically relevant levels. A physiologically relevant level is one which either approximates the level at which the product is produced in the body or results in improvement of the abnormal or undesirable condition. Cells administered in the present method are cells transfected with exogenous DNA which encodes a therapeutic product, exogenous DNA which is itself a therapeutic product or exogenous DNA, such as a regulatory sequence, which is introduced into a preselected site in genomic DNA through homologous recombination and functions to cause recipient cells to produce a product which is normally not expressed in the cells or to produce the product of a higher level than occurs in the corresponding nontransfected cell. In the embodiment in which a regulatory sequence (e.g., a promoter) is introduced, it replaces or disables a regulatory sequence normally associated with a gene, and results in expression of the gene at a higher level than occurs in the corresponding nontransfected cell or allows a pattern of regulation or induction that is different from the corresponding nontransfected cell.

Immortalized cells which produce a therapeutic protein produced by the methods described herein and in the related U.S. patent application Ser. Nos. 07/789,188, 07,911,533 and 07,787,840 (incorporated herein by reference), can be used in gene therapy whether made by cells produced by: 1) random integration of the therapeutic protein, 2) homologous recombination to target the therapeutic protein into a cell's genome, 3) homologous recombination to activate or turn on a gene of therapeutic interest, or 4) gene amplification in conjunction with one of the three preceding methods. According to the invention described herein, the immortalized cells are enclosed in one of a number of semipermeable barrier devices. The permeability properties of the device are such that the cells are prevented from leaving the device upon implantation into an animal, but the therapeutic product is freely permeable and can leave the barrier device and enter the local space surrounding the implant or enter the systemic circulation. A number of filtration membranes can be used for this purpose, including, but not limited to, cellulose, cellulose acetate, nitrocellulose, polysulfone, polyvinylidene difluoride, polyvinyl chloride polymers and polymers of polyvinyl chloride derivatives. Alternatively, barrier devices can be utilized to allow primary, secondary, or immortalized cells from another species to be used for gene therapy in humans. The use of cells from other species can be desirable in cases where the non-human cells are advantageous for protein production purposes or in cases where the non-human protein is therapeutically useful, for example, the use of cells derived from salmon for the production of salmon calcitonin and the use of cells derived from pigs for the production of porcine insulin.

Cells from non-human species can also be used for in vitro protein production. These cells can be immortalized, primary, or secondary cells which produce a therapeutic protein produced by the methods described here and in the U.S. patent applications incorporated herein by reference, whether made by cells produced by: 1) random integration of the therapeutic protein, 2) homologous recombination to target the therapeutic protein into a cell's genome, 3) homologous recombination to activate or turn on a gene of therapeutic interest, or 4) gene amplification in conjunction with one of the three preceding methods. The use of cells from other species may be desirable in cases where the non-human cells are advantageous for protein production purposes (for example CHO cells) or in cases where the non-human protein is therapeutically or commercially useful, for example, the use of cells derived from salmon for the production of salmon calcitonin, the use of cells derived from pigs for the production of porcine insulin, and the use of bovine cells for the production of bovine growth hormone.

Transfected cells of the present invention are useful in a number of applications in humans and animals. In one embodiment, the cells can be implanted into a human or an animal for protein delivery in the human or animal. For example, human growth hormone (hGH), human EPO (hEPO), or human insulinotropin can be delivered systemically in humans for therapeutic benefits. Barrier devices, through which the therapeutic product is freely permeable, can be used to retain cells in a fixed position in vivo or to protect and isolate the cells from the host's immune system. Barrier devices are particularly useful and allow transfected immortalized cells, transfected cells from another species (transfected xenogeneic cells), or cells from a nonhistocompatibility-matched donor (transfected allogeneic cells) to be implanted for treatment of human or animal conditions or for agricultural uses (i.e., meat and dairy production). Barrier devices also allow convenient short-term (i.e., transient) therapy by providing ready access to the cells for removal when the treatment regimen is to be halted for any reason.

Transfected cells of the present invention are also useful for eliciting antibody production or for immunizing humans and animals against pathogenic agents. Implanted transfected cells can be used to deliver immunizing antigens that result in stimulation of the host's cellular and humoral immune responses. These immune responses can be designed for protection of the host from future infectious agents (i.e., for vaccination), to stimulate and augment the disease-fighting capabilities directed against an ongoing infection, or to produce antibodies directed against the antigen produced in vivo by the transfected cells that can be useful for therapeutic or diagnostic purposes. Removable barrier devices can be used to allow a simple means of terminating exposure to the antigen. Alternatively, the use of cells that will ultimately be rejected (xenogeneic or allogeneic transfected cells) can be used to limit exposure to the antigen since antigen production will cease when the cells have been rejected.

Explanation of the Examples

As described herein, Applicants have demonstrated that DNA can be introduced into primary, secondary or immortalized vertebrate cells and integrated into the genome of the transfected primary or secondary cells by homologous recombination. That is, they have demonstrated gene targeting in primary, secondary and immortalized mammalian cells. They have further demonstrated that the exogenous DNA has the desired function in the homologously recombinant (HR) cells and that correctly targeted cells can be identified on the basis of a detectable phenotype conferred by the properly targeted DNA.

In addition, the present invention relates to a method of protein production using transfected primary, secondary or immortalized cells. The method involves transfecting primary cells, secondary cells or immortalized cells with exogenous DNA which encodes a therapeutic product or with DNA which is sufficient to target to and activate an endogenous gene which encodes a therapeutic product. For example, Examples 1g, 1j, 2, 3 and 4 describe protein production by targeting and activation of a selected endogenous gene.

The applicants also describe DNA constructs and methods for amplifying an endogenous cellular gene that has been activated by gene targeting (Examples 1f–1k and Example 3) and further describe methods by which a gene can be inserted at a preselected site in the genome of a primary, secondary, or immortalized cell by gene targeting (Example 1d).

Applicants describe construction of a plasmid useful for targeting to a particular locus (the HPRT locus) in the human genome and selection based upon a drug resistant phenotype (Example 1a). This plasmid is designated pE3Neo and its integration into the cellular genomes at the HPRT locus produces cells which have an hprt⁻, 6-TG resistant phenotype and are also G418 resistant. As described, they have shown that pE3Neo functions properly in gene targeting in an established human fibroblast cell line (Example 1b), by demonstrating localization of the DNA introduced into established cells within exon 3 of the HPRT gene.

In addition, Applicants demonstrate gene targeting in primary and secondary human skin fibroblasts using pE3Neo (Example 1c). The subject application further demonstrates that modification of DNA termini enhances targeting of DNA into genomic DNA (Examples 1c and 1e).

Examples 1f–1h and 2 illustrate embodiments in which the normal regulatory sequences upstream of the human EPO gene are altered to allow expression of hEPO in primary or secondary fibroblast strains which do not express EPO in detectable quantities in their untransfected state. In one embodiment the product of targeting leaves the normal EPO protein intact, but under the control of the mouse metallothionein promoter. Examples 1i and 1j demonstrate the use of similar targeting constructs to activate the endogenous growth hormone gene in primary or secondary human fibroblasts. In other embodiments described for activating EPO expression in human fibroblasts, the products of targeting events are chimeric transcription units, in which the first exon of the human growth hormone gene is positioned upstream of EPO exons 2–5. The product of transcription (controlled by the mouse metallothionein promoter), splicing, and translation is a protein in which amino acids 1–4 of the hEPO signal peptide are replaced with amino acid residues 1–3 of hGH. The chimeric portion of this protein, the signal peptide, is removed prior to secretion from cells. Example 5 describes targeting constructs and methods for producing cells which will convert a gene (with introns) into an expressible cDNA copy of that gene (without introns) and the recovery of such expressible cDNA molecules in microbial (e.g., yeast or bacterial) cells.

Figure 5:
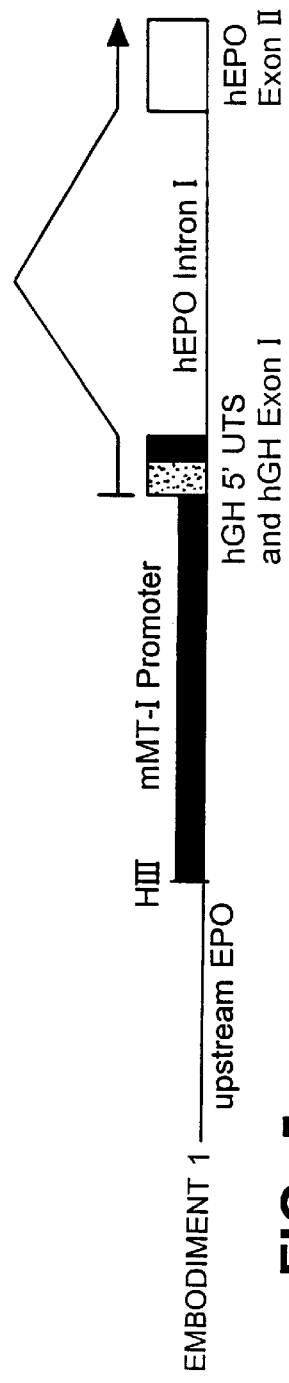
FIG. 5 is a schematic diagram of a strategy for transcriptionally activating the hEPO gene; the thin lines represent hEPO sequences; thick lines, mouse metallothionein I promoter; stippled box, 5' untranslated region of hGH; solid box, hGH exon 1; open boxes, hEPO coding sequences; HIII, HindIII site.
Figure 6:
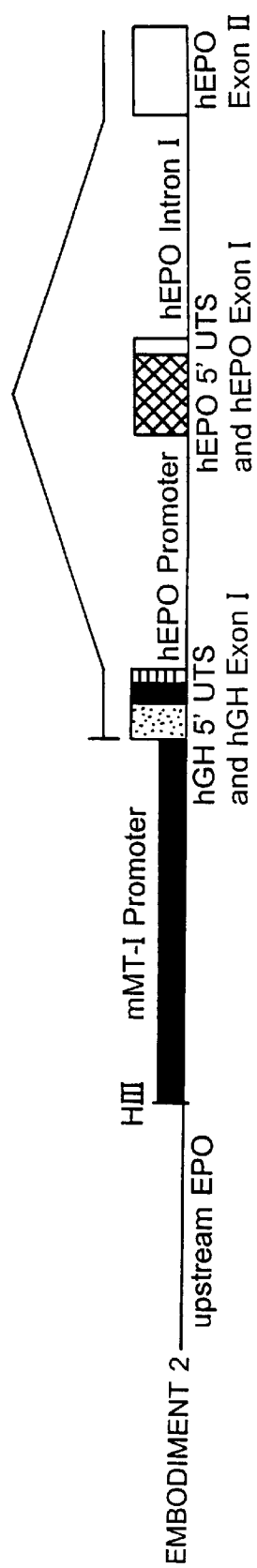
FIG. 6 is a schematic diagram of a strategy for transcriptionally activating the hEPO gene; the thin lines represent hEPO sequences; thick lines, mouse metallothionein I promoter; stippled box, 5' untranslated region of hGH; solid box, hGH exon 1; striped box, 10 bp linker from hEPO intron 1; cross-hatched box, 5' untranslated region of hEPO; and open boxes, hEPO coding sequences; HIII, HindIII site.

The Examples provide methods for activating or for activating and amplifying endogenous genes by gene targeting which do not require manipulation or other uses of the target genes' protein coding regions. By these methods, normally inactive genes can be activated in cells that have properties desirable for in vitro protein production (e.g., pharmaceutics) or in vivo protein delivery methods (e.g. gene therapy). FIGS. 5 and 6 illustrate two strategies for transcriptionally activating the hEPO gene.

Using the methods and DNA constructs or plasmids taught herein or modifications thereof which are apparent to one of ordinary skill in the art, exogenous DNA which encodes a therapeutic product (e.g., protein, ribozyme, nucleic acid) can be inserted at preselected sites in the genome of vertebrate (e.g., mammalian, both human and nonhuman) primary or secondary cells.

The present invention will now be illustrated by the following examples, which are not intended to be limiting in any way.

EXAMPLES

Example 1

Production of Transfected Cell Strains by Gene Targeting

Gene targeting occurs when transfecting DNA either integrates into or partially replaces chromosomal DNA sequences through a homologous recombinant event. While such events can occur in the course of any given transfection experiment, they are usually masked by a vast excess of events in which plasmid DNA integrates by nonhomologous, or illegitimate, recombination.

Examples 1a, 1b, 1e, 1f and 1i are reproduced from U.S. patent application Ser. No. 07/789,188, filed on Nov. 5, 1991, and incorporated herein by reference. These examples are presented here for background information.

a. Generation of a Construct Useful for Selection of Gene Targeting Events in Human Cells One approach to selecting the targeted events is by genetic selection for the loss of a gene function due to the integration of transfecting DNA. The human HPRT locus encodes the enzyme hypoxanthine-phosphoribosyl transferase. hprt⁻ cells can be selected for by growth in medium containing the nucleoside analog 6-thioguanine (6-TG): cells with the wild-type (HPRT+) allele are killed by 6-TG, while cells with mutant (hprt⁻) alleles can survive. Cells harboring targeted events which disrupt HPRT gene function are therefore selectable in 6-TG medium.

To construct a plasmid for targeting to the HPRT locus, the 6.9 kb HindIII fragment extending from positions 11,960-18,869 in the HPRT sequence (Genebank name HUMHPRTB; Edwards, A. et al., *Genomics* 6:593–608 (1990)) and including exons 2 and 3 of the HPRT gene, is subcloned into the HindIII site of pUC12. The resulting clone is cleaved at the unique XhoI site in exon 3 of the HPRT gene fragment and the 1.1 kb SalI-XhoI fragment containing the neo gene from pMC1Neo (Stratagene) is inserted, disrupting the coding sequence of exon 3. One orientation, with the direction of neo transcription opposite that of HPRT transcription was chosen and designated pE3Neo. The replacement of the normal HPRT exon 3 with the neo-disrupted version will result in an hprt⁻, 6-TG resistant phenotype. Such cells will also be G418 resistant.

b. Gene Targeting in an Established Human Fibroblast Cell Line

As a demonstration of targeting in immortalized cell lines, and to establish that pE3Neo functions properly in gene targeting, the human fibrosarcoma cell line HT1080 (ATCC CCL 121) was transfected with pE3Neo by electroporation.

HT1080 cells were maintained in HAT (hypoxanthine/aminopterin/xanthine) supplemented DMEM with 15% calf serum (Hyclone) prior to electroporation. Two days before electroporation, the cells are switched to the same medium without aminopterin. Exponentially growing cells were trypsinized and diluted in DMEM/15% calf serum, centrifuged, and resuspended in PBS (phosphate buffered saline) at a final cell volume of 13.3 million cells per ml. pE3Neo is digested with HindIII, separating the 8 kb HPRT-neo fragment from the pUC12 backbone, purified by phenol extraction and ethanol precipitation, and resuspended at a concentration of 600 μg/ml. 50 μl (30 μg) was added to the electroporation cuvette (0.4 cm electrode gap; Bio-Rad Laboratories), along with 750 μl of the cell suspension (10 million cells). Electroporation was at 450 volts, 250 μFarads (Bio-Rad Gene Pulser; Bio-Rad Laboratories). The contents of the cuvette were immediately added to DMEM with 15% calf serum to yield a cell suspension of 1 million cells per 25 ml media. 25 ml of the treated cell suspension was plated onto 150 mm diameter tissue culture dishes and incubated at 37° C, 5% $CO_2$. 24 hrs later, a G418 solution was added directly to the plates to yield a final concentration of 800 μg/ml G418. Five days later the media was replaced with DMEM/15% calf serum/800 μg/ml G418. Nine days after electroporation, the media was replaced with DMEM/15% calf serum/800 μg/ml G418 and 10 μM 6-thioguanine.

Colonies resistant to G418 and 6-TG were picked using cloning cylinders 14–16 days after the dual selection was initiated.

The results of five representative targeting experiments in HT1080 cells are shown in Table 1.

TABLE 1

| Transfection | Number of Treated Cells | Number of G418$^r$ 6-TG$^r$ Clones |
|---|---|---|
| 1 | $1 \times 10^7$ | 32 |
| 2 | $1 \times 10^7$ | 28 |
| 3 | $1 \times 10^7$ | 24 |
| 4 | $1 \times 10^7$ | 32 |
| 5 | $1 \times 10^7$ | 66 |

For transfection 5, control plates designed to determine the overall yield of G418$^r$ colonies indicated that 33,700 G418$^r$ colonies could be generated from the initial $1\times10^7$ treated cells. Thus, the ratio of targeted to non-targeted events is 66/33,700, or 1 to 510. In the five experiments combined, targeted events arise at a frequency of $3.6\times10^6$, or 0.00036% of treated cells.

Restriction enzyme and Southern hybridization experiments using probes derived from the neo and HPRT genes localized the neo gene to the HPRT locus at the predicted site within HPRT exon 3.

c. Gene Targeting in Primary and Secondary Human Skin Fibroblasts pE3Neo is digested with HindIII, separating the 8 kb HPRT-neo fragment from the pUC12 backbone, and purified by phenol extraction and ethanol precipitation. DNA was resuspended at 2 mg/ml. Three million secondary human foreskin fibroblasts cells in a volume of 0.5 ml were electroporated at 250 volts and 960 µgFarads, with 100 µg of HindIII pE3Neo (50 µl). Three separate transfections were performed, for a total of 9 million treated cells. Cells are processed and selected for G418 resistance. 500,000 cells per 150 mm culture dish were plated for G418 selection. After 10 days under selection, the culture medium is replaced with human fibroblast nutrient medium containing 400 µg/ml G418 and 10 µM 6-TG. Selection with the two drug combination is continued for 10 additional days. Plates are scanned microscopically to localize human fibroblast colonies resistant to both drugs. The fraction of G418$^r$ t-TG$^r$ colonies is 4 per 9 million treated cells. These colonies constitute 0.0001% (or 1 in a million) of all cells capable of forming colonies. Control plates designed to determine the overall yield of G418$^r$ colonies indicated that 2,850 G418$^r$ colonies could be generated from the initial $9\times10^6$ treated cells. Thus, the ratio of targeted to non-targeted events is 4/2,850, or 1 to 712. Restriction enzyme and Southern hybridization experiments using probes derived from the neo and HPRT genes were used to localize the neo gene to the HPRT locus at the predicted site within HPRT exon 3 and demonstrate that targeting had occurred in these four clonal cell strains. Colonies resistant to both drugs have also been isolated by transfecting primary cells ($1/3.0\times10^7$).

The results of several pE3Neo targeting experiments are summarized in Table 2. HindIII digested pE3Neo was either transfected directly or treated with exonuclease III to generate 5' single-stranded overhangs prior to transfection (see Example 1c). DNA preparations with single-stranded regions ranging from 175 to 930 base pairs in length were tested. Using pE3neo digested with HindIII alone, 1/799 G418-resistant colonies were identified by restriction enzyme and Southern hybridization analysis as having a targeted insertion of the neo gene at the HPRT locus (a total of 24 targeted clones were isolated). Targeting was maximally stimulated (approximately 10-fold stimulation) when overhangs of 175 bp were used, with 1/80 G418$^r$ colonies displaying restriction fragments that are diagnostic for targeting at HPRT (a total of 9 targeted clones were isolated). Thus, using the conditions and recombinant DNA constructs described here, targeting is readily observed in normal human fibroblasts and the overall targeting frequency (the number of targeted clones divided by the total number of clones stably transfected to G418-resistance) can be stimulated by transfection with targeting constructs containing single-stranded overhanging tails, by the method as described in Example 1e.

TABLE 2

TARGETING TO THE HPRT LOCUS IN HUMAN FIBROBLASTS

| pE3neo Treatment | Number of Experiments | Number Targeted Per G418$^r$ Colony | Total Number of Targeted Clone |
|---|---|---|---|
| HindIII digest | 6 | 1/799 | 24 |
| 175 bp overhang | 1 | 1/80 | 9 |
| 350 bp overhang | 3 | 1/117 | 20 |
| 930 bp overhang | 1 | 1/144 | 1 | d. Generation of a Construct for Targeted Insertion of a Gene of Therapeutic Interest Into the Human Genome and Its Use in Gene Targeting A variant of pE3Neo, in which a gene of therapeutic interest is inserted within the HPRT coding region, adjacent to or near the neo gene, can be used to target a gene of therapeutic interest to a specific position in a recipient primary or secondary cell genome. Such a variant of pE3Neo can be constructed for targeting the hGH gene to the HPRT locus.

pXGH5 (schematically presented in FIG. 1) is digested with EcoRI and the 4.1 kb fragment containing the hGH gene and linked mouse metallothionein (mMT) promoter is isolated. The EcoRI overhangs are filled in with the Klenow fragment from E. coli DNA polymerase. Separately, pE3Neo is digested with XhoI, which cuts at the junction of the neo fragment and HPRT exon 3 (the 3' junction of the insertion into exon 3). The XhoI overhanging ends of the linearized plasmid are filled in with the Klenow fragment from E. coli DNA polymerase, and the resulting fragment is ligated to the 4.1 kb blunt-ended hGH-mMT fragment. Bacterial colonies derived from the ligation mixture are screened by restriction enzyme analysis for a single copy insertion of the hGH-mMT fragment and one orientation, the hGH gene transcribed in the same direction as the neo gene, is chosen and designated pE3Neo/hGH. pE3Neo/hGH is digested with HindIII, releasing the 12.1 kb fragment containing HPRT, neo and mMT-hGH sequences. Digested DNA is treated and transfected into primary or secondary human fibroblasts as described in Example 1c. G418$^r$ TG$^r$ colonies are selected and analyzed for targeted insertion of the mMT-hGH and neo sequences into the HPRT gene as described in Example 1c. Individual colonies are assayed for hGH expression using a commercially available immunoassay (Nichols Institute).

Figure 4:
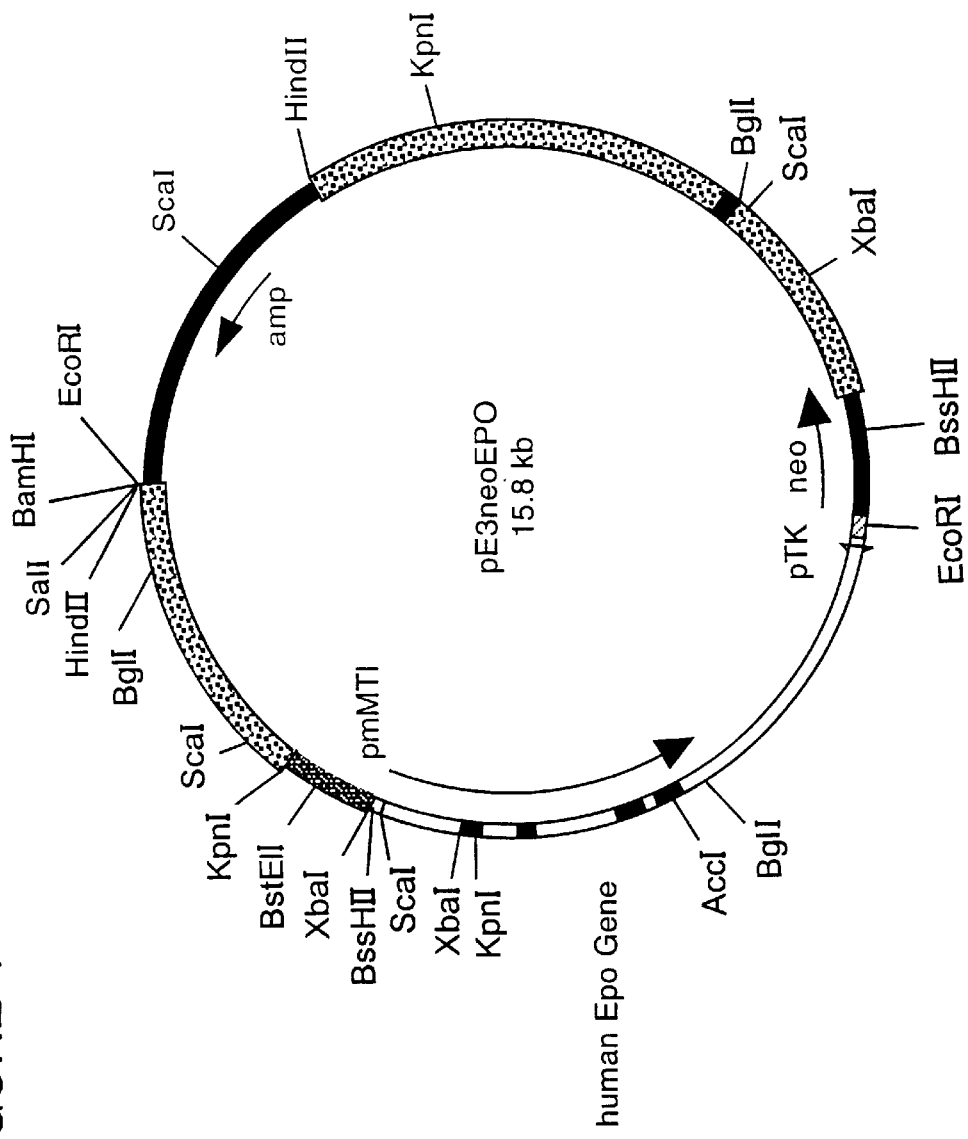
FIG. 4 is a schematic representation of plasmid PE3neoEPO. The positions of the human erythropoietin gene and the neo and amp resistance genes are indicated. Arrows indicate the directions of transcription of the various genes. pmMT1 denotes the mouse metallothionein promoter (driving hEPO expression) and pTK denotes the Herpes Simplex Virus thymidine kinase promoter (driving neo expression). The dotted regions of the map mark the positions of human HPRT sequences. The relative positions of restriction endonuclease recognition sites are indicated.

Secondary human fibroblasts were transfected with pE3Neo/hGH and thioguanine-resistant colonies were analyzed for stable hGH expression and by restriction enzyme and Southern hybridization analysis. Of thirteen TG$^r$ colonies analyzed, eight colonies were identified with an insertion of the hGH gene into the endogenous HPRT locus. All eight strains stably expressed significant quantities of hGH, with an average expression level of 22.7 µg/$10^6$ cells/24 hours. Alternatively, plasmid pE3neoEPO, FIG. 4, may be used to target EPO to the human HPRT locus.

The use of homologous recombination to target a gene of therapeutic interest to a specific position in a cell's genomic DNA can be expanded upon and made more useful for producing products for therapeutic purposes (e.g., pharmaceutics, gene therapy) by the insertion of a gene through which cells containing amplified copies of the gene can be selected for by exposure of the cells to an appropriate drug selection regimen. For example, pE3neo/hGH (Example 1d) can be modified by inserting the dhfr, ada, or CAD gene at a position immediately adjacent to the hGH or neo genes in pE3neo/hGH. Primary, secondary, or immortalized cells are transfected with such a plasmid and correctly targeted events are identified. These cells are further treated with increasing concentrations of drugs appropriate for the selection of cells containing amplified genes (for dhfr, the selective agent is methotrexate, for CAD the selective agent is N-(phosphonacetyl)-L-aspartate (PALA), and for ada the selective agent is an adenine nucleoside (e.g., alanosine). In this manner the integration of the gene of therapeutic interest will be coamplified along with the gene for which amplified copies are selected. Thus, the genetic engineering of cells to produce genes for therapeutic uses can be readily controlled by preselecting the site at which the targeting construct integrates and at which the amplified copies reside in the amplified cells.

e. Modification of DNA Termini to Enhance Targeting

Several lines of evidence suggest that 3'-overhanging ends are involved in certain homologous recombination pathways of *E. coli,* bacteriophage, *S. cerevisiae* and *Xenopus laevis.* In Xenopus laevis oocytes, molecules with 3'-overhanging ends of several hundred base pairs in length underwent recombination with similarly treated molecules much more rapidly after microinjection than molecules with very short overhangs (4 bp) generated by restriction enzyme digestion. In yeast, the generation of 3'-overhanging ends several hundred base pairs in length appears to be a rate limiting step in meiotic recombination. No evidence for an involvement of 3'-overhanging ends in recombination in human cells has been reported, and in no case have modified DNA substrates of any sort been shown to promote targeting (one form of homologous recombination) in any species. In human cells, the effect of 3'-overhanging ends on targeting is untested. The experiment described in the following example and Example 1c suggests that 5'-overhanging ends are effective for stimulating targeting in primary, secondary and immortalized human fibroblasts.

There have been no reports on the enhancement of targeting by modifying the ends of the transfecting DNA molecules. This example serves to illustrate that modification of the ends of linear DNA molecules, by conversion of the molecules' termini from a double-stranded form to a single-stranded form, can stimulate targeting into the genome of primary and secondary human fibroblasts.

1100 µg of plasmid pE3Neo (Example 1a) is digested with HindIII. This DNA can be used directly after phenol extraction and ethanol precipitation, or the 8 kb HindIII fragment containing only HPRT and the neo gene can be separated away from the pUC12 vector sequences by gel electrophoresis. ExoIII digestion of the HindIII digested DNA results in extensive exonucleolytic digestion at each end, initiating at each free 3' end, and leaving 5'-overhanging ends. The extent of exonucleolytic action and, hence, the length of the resulting 5'-overhangs, can be controlled by varying the time of ExoIII digestion. ExoIII digestion of 100 µg of HindIII digested pE3Neo is carried out according to the supplier's recommended conditions, for times of 30 sec, 1 min, 1.5 min, 2 min, 2.5 min, 3 min, 3.5 min, 4 min, 4.5 min, and 5 min. To monitor the extent of digestion an aliquot from each time point, containing 1 µg of ExoIII treated DNA, is treated with mung bean nuclease (Promega), under conditions recommended by the supplier, and the samples fractionated by gel electrophoresis. The difference in size between non-treated, HindIII digested pE3Neo and the same molecules treated with ExoIII and mung bean nuclease is measured. This size difference divided by two gives the average length of the 5'-overhang at each end of the molecule. Using the time points described above and digestion at 30°, the 5'-overhangs produced should range from 100 to 1,000 bases.

60 µg of ExoIII treated DNA (total HindIII digest of pE3Neo) from each time point is purified and electroporated into primary, secondary, or immortalized human fibroblasts under the conditions described in Example 1c. The degree to which targeting is enhanced by each ExoIII treated preparation is quantified by counting the number of $G418^r$ $6\text{-}TG^r$ colonies and comparing these numbers to targeting with HindIII digested pE3Neo that was not treated with ExoIII.

The effect of 3'-overhanging ends can also be quantified using an analogous system. In this case HindIII digested pE3Neo is treated with bacteriophage T7 gene 6 exonuclease (United States Biochemicals) for varying time intervals under the supplier's recommended conditions. Determination of the extent of digestion (average length of 3'-overhang produced per end) and electroporation conditions are as described for ExoIII treated DNA. The degree to which targeting is enhanced by each T7 gene 6 exonuclease treated preparation is quantified by counting the number of $G418^r$ $6\text{-}TG^r$ colonies and comparing these numbers to targeting with HindIII digested pE3Neo that was not treated with T7 gene 6 exonuclease.

Other methods for generating 5' and 3' overhanging ends are possible, for example, denaturation and annealing of two linear molecules that partially overlap with each other will generate a mixture of molecules, each molecule having 3'-overhangs at both ends or 5'-overhangs at both ends, as well as reannealed fragments indistinguishable from the starting linear molecules. The length of the overhangs is determined by the length of DNA that is not in common between the two DNA fragments.

f. Construction of Targeting Plasmids for Placing the Human Erythropoietin Gene Under the Control of the Mouse Metallothionein Promoter in Primary, Secondary and Immortalized Human Fibroblasts The following serves to illustrate one embodiment of the present invention, in which the normal positive and negative regulatory sequences upstream of the human erythropoietin (EPO) gene are altered to allow expression of human erythropoietin in primary, secondary or immortalized human fibroblasts, which do not express EPO in significant quantities as obtained.

A region lying exclusively upstream of the human EPO coding region can be amplified by PCR. Three sets of primers useful for this purpose were designed after analysis of the published human EPO [Genbank designation HUMERPA; Lin, F-K., et al., *Proc. Natl. Acad. Sci., USA* 82:7580–7584 (1985)]. These primer pairs can amplify fragments of 609, 603, or 590 bp.

TABLE 3

| Primer | HUMERPA Coordinate | Sequence | Fragment Size |
|---|---|---|---|
| F1 | 2→20 | 5'AGCTTCTGGGCTTCCAGAC (SEQ ID NO 1) | |
| R2 | 610→595 | 5'GGGGTCCCTCAGCGAC (SEQ ID NO 2) | 609 bp |
| F2 | 8→24 | 5'TGGGCTTCCAGACCCAG (SEQ ID NO 3) | |
| R2 | 610→595 | 5'GGGGTCCCTCAGCGAC (SEQ ID NO 2) | 603 bp |
| F3 | 21→40 | 5'CCAGCTACTTTGCGGAACTC (SEQ ID NO 4) | |
| R2 | 610→595 | 5'GGGGTCCCTCAGCGAC (SEQ ID NO 2) | 590 bp |

The three fragments overlap substantially and are interchangeable for the present purposes. The 609 bp fragment, extending from −623 to −14 relative to the translation start site (HUMERPA nucleotide positions 2 to 610), is ligated at both ends with ClaI linkers. The resulting ClaI-linked fragment is digested with ClaI and inserted into the ClaI site of pBluescriptIISK/+ (Stratagene), with the orientation such that HUMERPA nucleotide position 610 is adjacent to the SalI site in the plasmid polylinker). This plasmid, p5'EPO, can be cleaved, separately, at the unique FspI or SfiI sites in the EPO upstream fragment (HUMERPA nucleotide positions 150 and 405, respectively) and ligated to the mouse metallothionein promoter. Typically, the 1.8 kb EcoRI-BglII from the mMT-I gene [containing no mMT coding sequences; Hamer, D. H. and Walling M., *J. Mol. Appl. Gen*, 1:273 288 (1982); this fragment can also be isolated by known methods from mouse genomic DNA using PCR primers designed from analysis of mMT sequences available from Genbank; i.e., MUSMTI, MUSMTIP, MUSMTIPRM] is made blunt-ended by known methods and ligated with SfiI digested (also made blunt-ended) or FspI digested p5'EPO. The orientations of resulting clones are analyzed and those in which the former mMT BglII site is proximal to the SalI site in the plasmid polylinker are used for targeting primary and secondary human fibroblasts. This orientation directs mMT transcription towards HUMERPA nucleotide position 610 in the final construct. The resulting plasmids are designated p5'EPO-mMTF and p5'EPO-mMTS for the mMT insertions in the FspI and SfiI sites, respectively.

Additional upstream sequences are useful in cases where it is desirable to modify, delete and/or replace negative regulatory elements or enhancers that lie upstream of the initial target sequence. In the case of EPO, a negative regulatory element that inhibits EPO expression in extrahepatic and extrarenal tissues [Semenza, G. L. et al., *Mol. Cell. Biol.* 10:930–938 (1990)] can be deleted. A series of deletions within the 6 kb fragment are prepared. The deleted regions can be replaced with an enhancer with broad host-cell activity [e.g. an enhancer from the Cytomegalovirus (CMV)].

The orientation of the 609 bp 5'EPO fragment in the pBluescriptIISK/+ vector was chosen since the HUMERPA sequences are preceded on their 5' end by a BamHI (distal) and HindIII site (proximal). Thus, a 6 kb BamHI-HindIII fragment normally lying upstream of the 609 bp fragment (Semenza, G. L. et al., *Mol. Cell. Biol.* 10:930–938 (1990)) can be isolated from genomic DNA by known methods. For example, a bacteriophage, cosmid, or yeast artificial chromosome library could be screened with the 609 bp PCR amplified fragment as a probe. The desired clone will have a 6 kb BamHI-HindIII fragment and its identity can be confirmed by comparing its restriction map from a restriction map around the human EPO gene determined by known methods. Alternatively, constructing a restriction map of the human genome upstream of the EPO gene using the 609 bp fragment as a probe can identify enzymes which generate a fragment originating between HUMERPA coordinates 2 and 609 and extending past the upstream BamHI site; this fragment can be isolated by gel electrophoresis from the appropriate digest of human genomic DNA and ligated into a bacterial or yeast cloning vector. The correct clone will hybridize to the 609 bp 5'EPO probe and contain a 6 kb BamHI-HindIII fragment. The isolated 6 kb fragment is inserted in the proper orientation into p5'EPO, p5'EPO-mMTF, or p5'EPO-mMTS (such that the HindIII site is adjacent to HUMERPA nucleotide position 2). Additional upstream sequences can be isolated by known methods, using chromosome walking techniques or by isolation of yeast artificial chromosomes hybridizing to the 609 bp 5'EPO probe.

The cloning strategies described above allow sequences upstream of EPO to be modified in vitro for subsequent targeted transfection of primary, secondary or immortalized human fibroblasts. The strategies describe simple insertions of the mMT promoter, as well as deletion of the negative regulatory region, and deletion of the negative regulatory region and replacement with an enhancer with broad host-cell activity.

g. Targeting to Sequences Flanking the Human EPO Gene and Isolation of Targeted Primary, Secondary and Immortalized Human Fibroblasts by Screening For targeting, the plasmids are cut with restriction enzymes that free the insert away from the plasmid backbone. In the case of p5'EPO-mMTS, HindIII and SalI digestion releases a targeting fragment of 2.4 kb, comprised of the 1.8 kb mMT promoter flanked on the 5' and 3' sides by 405 bp and 204 base pairs, respectively, of DNA for targeting this construct to the regulatory region of the EPO gene. This DNA or the 2.4 kb targeting fragment alone is purified by phenol extraction and ethanol precipitation and transfected into primary or secondary human fibroblasts under the conditions described in Example 1c. Transfected cells are plated onto 150 mm dishes in human fibroblast nutrient medium. 48 hours later the cells are plated into 24 well dishes at a density of 10,000 cells/cm$^2$ [approximately 20,000 cells per well; if targeting occurs at a rate of 1 event per $10^6$ clonable cells (Example 1c, then about 50 wells would need to be assayed to isolate a single expressing colony]. Cells in which the transfecting DNA has targeted to the homologous region upstream of EPO will express EPO under the control of the mMT promoter. After 10 days, whole well supernatants are assayed for EPO expression using a commercially available immunoassay kit (Amgen). Clones from wells displaying EPO synthesis are isolated using known methods, typically by assaying fractions of the heterogenous populations of cells separated into individual wells or plates, assaying fractions of these positive wells, and repeating as needed, ultimately isolating the targeted colony by screening 96-well microtiter plates seeded at one cell per well. DNA from entire plate lysates can also be analyzed by PCR for amplification of a fragment using a mMT specific primer in conjunction with a primer lying upstream of HUMERPA nucleotide position 1. This primer pair should amplify a DNA fragment of a size precisely predicted based on the DNA sequence. Positive plates are trypsinized and replated at successively lower dilutions, and the DNA preparation and PCR steps repeated as needed to isolate targeted cells.

The targeting schemes herein described can also be used to activate hGH expression in immortalized human cells (for example, HT1080 fibroblasts, HeLa cells, MCF-7 breast cancer cells, K-562 leukemia cells, KB carcinoma cells or 2780AD ovarian carcinoma cells) for the purposes of producing hGH for conventional pharmaceutic delivery.

h. Targeting to Sequences Flanking the Human EPO Gene and Isolation of Targeted Primary, Secondary and Immortalized Human Fibroblasts by a Positive or a Combined Positive/Negative Selection System The strategy for constructing p5'EPO-mMTF, p5'EPO-mMTS, and derivatives of such with the additional upstream 6 kb BamHI-HindIII fragment can be followed with the additional step of inserting the neo gene adjacent to the mMT promoter. In addition, a negative selection marker, for example, gpt (from PMSG (Pharmacia) or another suitable source], can be inserted adjacent to the HUMERPA sequences in the pBluescriptIISK/+ polylinker. In the former case, G418$^r$ colonies are isolated and screened by PCR amplification or restriction enzyme and Southern hybridization analysis of DNA prepared from pools of colonies to identify targeted colonies. In the latter case, G418$^r$ colonies are placed in medium containing 6-thioxanthine to select against the integration of the gpt gene [Besnard, C. et al., *Mol. Cell. Biol.* 7:4139–4141 (1987)]. In addition, the HSV-TK gene can be placed on the opposite side of the insert as gpt, allowing selection for neo and against both gpt and TK by growing cells in human fibroblast nutrient medium containing 400 $\mu$g/ml G418, 100 $\mu$M 6-thioxanthine, and 25 $\mu$g/ml gancyclovir. The double negative selection should provide a nearly absolute selection for true targeted events and Southern blot analysis provides an ultimate confirmation.

The targeting schemes herein described can also be used to activate hEPO expression in immortalized human cells (for example, HT1080 fibroblasts, HeLa cells, MCF-7 breast cancer cells, K-562 leukemia cells, KB carcinoma cells or 2780AD ovarian carcinoma cells) for the purposes of producing hEPO for conventional pharmaceutic delivery.

i. Construction of Targeting Plasmids for Placing the Human Growth Hormone Gene Under the Control of the Mouse Metallothione in Promoter in Primary, Secondary or Immortalized Human Fibroblasts The following example serves to illustrate one embodiment of the present invention, in which the normal regulatory sequences upstream of the human growth hormone gene are altered to allow expression of human growth hormone in primary, secondary or immortalized human fibroblasts.

Targeting molecules similar to those described in Example if for targeting to the EPO gene regulatory region are generated using cloned DNA fragments derived from the 5' end of the human growth hormone N gene. An approximately 1.8 kb fragment spanning HUMGHCSA (Genbank Entry) nucleotide positions 3787–5432 (the positions of two EcoNI sites which generate a convenient sized fragment for cloning or for diagnostic digestion of subclones involving this fragment) is amplified by PCR primers designed by analysis of the HUMGHCSA sequence in this region. This region extends from the middle of hGH gene N intron 1 to an upstream position approximately 1.4 kb 5' to the translational start site. pUC12 is digested with EcoRI and BamHI, treated with Klenow to generate blunt ends, and recircularized under dilute conditions, resulting in plasmids which have lost the EcoRI and BamHI sites. This plasmid is designated pUC12XEB. HindIII linkers are ligated onto the amplified hGH fragment and the resulting fragment is digested with HindIII and ligated to HindIII digested pUC12XEB. The resulting plasmid, pUC12XEB-5'hGH, is digested with EcoRI and BamHI, to remove a 0.5 kb fragment lying immediately upstream of the hGH transcriptional initiation site. The digested DNA is ligated to the 1.8 kb EcoRI-BglII from the mMT-I gene [containing no mMT coding sequences; Hamer, D. H. and Walling, M., *J. Mol. Appl. Gen.* 1:273–288 (1982); the fragment can also be isolated by known methods from mouse genomic DNA using PCR primers designed from analysis of mMT sequences available from Genbank; i.e., MUSMTI, MUSMTIP, MUSMTIPRM]. This plasmid p5'hGH-mMT has the mMT promoter flanked on both sides by upstream hGH sequences.

The cloning strategies described above allow sequences upstream of hGH to be modified in vitro for subsequent targeted transfection of primary, secondary or immortalized human fibroblasts. The strategy described a simple insertion of the mMT promoter. Other strategies can be envisioned, for example, in which an enhancer with broad host-cell specificity is inserted upstream of the inserted mMT sequence.

j. Targeting to Sequences Flanking the Human hGH Gene and Isolation of Targeted Primary, Secondary and Immortalized Human Fibroblasts by Screening For targeting, the plasmids are cut with restriction enzymes that free the insert away from the plasmid backbone. In the case of p5'hGH-mMT, HindIII digestion releases a targeting fragment of 2.9 kb, comprised of the 1.8 kb mMT promoter flanked on the 5' end 3' sides by DNA for targeting this construct to the regulatory region of the hGH gene. This DNA or the 2.9 kb targeting fragment alone is purified by phenol extraction and ethanol precipitation and transfected into primary or secondary human fibroblasts under the conditions previously described in related U.S. patent application, Ser. Nos. 07/787,840 and 07/911,533. Transfected cells are plated onto 150 mm dishes in human fibroblast nutrient medium. 48 hours later the cells are plated into 24 well dishes at a density of 10,000 cells/cm$^2$ [approximately 20,000 cells per well; if targeting occurs at a rate of 1 event per 10$^6$ clonable cells (Example 1c), then about 50 wells would need to be assayed to isolate a single expressing colony]. Cells in which the transfecting DNA has targeted to the homologous region upstream of hGH will express hGH under the control of the mMT promoter. After 10 days, whole well supernatants are assayed for hGH expression using a commercially available immunoassay kit (Nichols). Clones from wells displaying hGH synthesis are isolated using known methods, typically by assaying fractions of the heterogenous populations of cells separated into individual wells or plates, assaying fractions of these positive wells, and repeating as needed, ultimately isolated the targeted colony by screening 96-well microtiter plates seeded at one cell per well. DNA from entire plate lysates can also be analyzed by PCR for amplification of a fragment using a mMT specific primer in conjunction with a primer lying downstream of HUMGHCSA nucleotide position 5,432. This primer pair should amplify a DNA fragment of a size precisely predicted based on the DNA sequence. Positive plates are trypsinized and replated at successively lower dilutions, and the DNA preparation and PCR steps repeated as needed to isolate targeted cells.

The targeting schemes herein described can also be used to activate hGH expression in immortalized human cells (for example, HT1080 fibroblasts, HeLa cells, MCF-7 breast cancer cells, K-562 leukemia cells, KB carcinoma cells or 2780AD ovarian carcinoma cells) for the purposes of producing hGH for conventional pharmaceutic delivery.

k. Targeting to Sequences Flanking the Human hGH Gene and Isolation of Targeted Primary, Secondary and Immortalized Human Fibroblasts by a Positive or a Combined Positive/negative Selection System The strategy for constructing p5'hGH-mMT can be followed with the additional step of inserting the neo gene adjacent to the mMT promoter. In addition, a negative selection marker, for example, gpt [from pMSG (Pharmacia) or another suitable source], can be inserted adjacent to the HUMGHCSA sequences in the pUC12 poly-linker. In the former case, G418$^r$ colonies are isolated and screened by PCR amplification or restriction enzyme and Southern hybridization analysis of DNA prepared from pools of colonies to identify targeted colonies. In the latter case, G418$^r$ colonies are placed in medium containing thioxanthine to select against the integration of the gpt gene (Besnard, C. at al., *Mol. Cell. Biol.* 7: 4139–4141 (1987)). In addition, the HSV-TK gene can be placed on the opposite side of the insert as gpt, allowing selection for neo and against both gpt and TK by growing cells in human fibroblast nutrient medium containing 400 µg/ml G418, 100 µM 6-thioxanthine, and 25 µg/ml gancyclovir. The double negative selection should provide a nearly absolute selection for true targeted events. Southern hybridization analysis is confirmatory.

The targeting schemes herein described can also be used to activate hGH expression in immortalized human cells (for example, HT1080 fibroblasts, HeLa cells, MCF-7 breast cancer cells, K-562 leukemia cells, KB carcinoma cells or 2780AD ovarian carcinoma cells) for the purposes of producing hGH for conventional pharmaceutic delivery.

The targeting constructs described in Examples 1f and 1i, and used in Examples 1g, 1h, 1j and 1k can be modified to include an amplifiable selectable marker (e.g., ada, dhfr, or CAD) which is useful for selecting cells in which the activated endogenous gene, and the amplifiable selectable marker, are amplified. Such cells, expressing or capable of expressing the endogenous gene encoding a therapeutic product can be used to produce proteins (e.g., hGH and hEPO) for conventional pharmaceutic delivery or for gene therapy.

growth hormone gene is positioned upstream of EPO exons 2–5. The product of transcription, splicing and translation is a protein in which amino acids 1–4 of the hEPO signal peptide are replaced with amino acid residues 1–3 of hGH. The two embodiments differ with respect to both the relative positions of the foreign regulatory sequences that are inserted and the specific pattern of splicing that needs to occur to produce the final, processed transcript.

Plasmid pXEPO-10 is designed to replace exon 1 of hEPO with exon 1 of hGH by gene targeting to the endogenous hEPO gene on human chromosome 7. Plasmid pXEPO-10 is constructed as follows. First, the intermediate plasmid pT163 is constructed by inserting the 6 kb HindIII-BamHI fragment (see Example if) lying upstream of the hEPO coding region into HindIII-BamHI digested pBluescriptII SK+ (Stratagene, LaJola, Calif.). The product of this ligation is digested with XhoI and HindIII and ligated to the 1.1 kb HindIII-XhoI fragment from pMClneoPolyA (Thomas, K. R. and Capecchi, M. R. *Cell* 51: 503–512 (1987) available from Strategene, LaJola, Calif. to create pT163. Oligonucleotides 13.1–13.4 are utilized in polymerase chain reactions to generate a fusion fragment in which the mouse metallothionein 1 (mMT-I) promoter—hGH exon 1 sequences are additionally fused to hEPO intron 1 sequences. First, oligonucleotides 13.1 and 13.2 are used to amplify the approximately 0.73 kb mMT-I promoter—hGH exon 1 fragment from pXGH5 (FIG. 1). Next, oligonucleotides 13.3 and 13.4 are used to amplify the approximately 0.57 kb fragment comprised predominantly of hEPO intron 1 from human genomic DNA. Finally, the two amplified fragments are mixed and further amplified with oligonucleotides 13.1 and 13.4 to generate the final fusion fragment (fusion fragment 3) flanked by a SalI site at the 5' side of the mMT-I moiety and an XhoI site at the 3' side of the hEPO intron 1 sequence. Fusion fragment 3 is digested with XhoI and SalI and ligated to XhoI digested pT163. The ligation mixture is transformed into *E. coli* and a clone containing a single insert of fusion fragment 3 in which the XhoI site is regenerated at the 3' side of hEPO intron 1 sequences is identified and designated pXEPO-10.

```
13.1 5' AAAAGTCGAC GGTACCTTGG TTTTTAAAAC CAGCCTGGAG      (SEQ ID NO 5)
            SalI   KpnI 13.2 5' CCTAGCGGCA ATGGCTACAG GTGAGTACTC GCGGGCTGGG CG   (SEQ ID NO 6)

13.3 5' CGCCCAGCCC GCGAGTACTC ACCTGTAGCC ATTGCCGCTA GG   (SEQ ID NO 7)

13.4 5' TTTTCTCGAG CTAGAACAGA TAGCCAGGCT GAGAG           (SEQ ID NO 8)
            XhoI
```

Example 2

Construction of Targeting Plasmids Which Result in Chimeric Transcription Units in Which Human Growth Hormone and Erythropoietin Sequences are Fused The following serves to illustrate two further embodiments of the present invention, in which the normal regulatory sequences upstream of the human EPO gene are altered to allow expression of hEPO in primary or secondary fibroblast strains which do not express EPO in detectable quantities in their untransfected state as obtained. In these embodiments, the products of the targeting events are chimeric transcription units in which the first exon of the human The non-boldface region of oligo 13.1 is identical to the MMT-I promoter, with the natural KpnI site as its 5' boundary. The boldface type denotes a SalI site tail to convert the 5' boundary to a SalI site. The boldface region of oligos 13.2 and 13.3 denote hGH sequences, while the non-boldface regions are intron 1 sequences from the hEPO gene. The non-boldface region of oligo 13.4 is identical to last 25 bases of hEPO intron 1. The boldface region includes an XhoI site tail to convert the 3' boundary of the amplified fragment to an XhoI site.

Plasmid pXEPO-11 is designed to place, by gene targeting, the MMT-I promoter and exon 1 of hGH upstream of the hEPO structural gene and promoter region at the endogenous hEPO locus on human chromosome 7. Plasmid pXEPO-11 is constructed as follows oligonucleotides 13.1 and 13.5–13.7 are utilized in polymerase chain reactions to generate a fusion fragment in which the mouse metallothionein I (mMT-I) promoter—hGH exon 1 sequences are additionally fused to hEPO sequences from −1 to −630 relative to the hEPO coding region. First, oligonucleotides 13.1 and 13.5 are used to amplify the approximately 0.73 kb mMT-I promoter—hGH exon 1 fragment from pXGH5 (FIG. 1). Next, oligonucleotides 13.6 and 13.7 are used to amplify, from human genomic DNA, the approximately 0.62 kb fragment comprised predominantly of hEPO sequences from −1 to −620 relative to the hEPO coding region. Both oligos 13.5 and 13.6 contain a 10 bp linker sequence located at the hGH intron 1—hEPO promoter region, which corresponds to the natural hEPO intron 1 splice donor site. Finally, the two amplified fragments are mixed and further amplified with oligonucleotides 13.1 and 13.7 to generate the final fusion fragment (fusion fragment 6) flanked by a SalI site at the 5' side of the mMT-I moiety and an XhoI site at the 3' side of the hEPO promoter region. Fusion fragment 6 is digested with XhoI and SalI and ligated to XhoI digested pT163. The ligation mixture is transformed into *E. coli* and a clone containing a single insert of fusion fragment 6 in which the XhoI site is regenerated at the 3' side of hEPO promoter sequences is identified and designated pXEPO-11.

Non-hEPO sequences in targeting fragment 1 are joined to hEPO sequences down-stream of hEPO intron 1. The replacement of the normal hEPO regulatory region with the mMT-I promoter will activate the EPO gene in fibroblasts, which do not normally express EPO. The replacement of hEPO exon 1 with hGH exon 1 results in a protein in which the first 4 amino acids of the hEPO signal peptide are replaced with amino acids 1–3 of hGH, creating a functional, chimeric signal peptide which is removed by post-translation processing from the mature protein and is secreted from the expressing cells.

Plasmid pXEPO-11 can be used for gene targeting by digestion with BamHI and XhoI to release the 7.4 kb fragment containing the mMT-I/hGH fusion flanked on both sides by hEPO sequences. This fragment (targeting fragment 2) contains no hEPO coding sequences, having only sequences lying between −1 and approximately −6620 upstream of the hEPO coding region to direct targeting to the human EPO locus. Targeting fragment 2 is transfected into primary or secondary human skin fibroblasts using conditions similar to those described in Example 1 g. G418-resistant colonies are picked into individual wells of 96-well plates and screened for EPO expression by an ELISA assay (R&D Systems, Minneapolis, Minn.). Cells in which the transfecting DNA integrates randomly into the human genome cannot produce EPO. Cells in which the transfect-

```
13.5 5'  CCTAGCGGCA ATGGCTACAG GTGAGTACTC AAGCTTCTGG GCTTCCAGAC CCAG    (SEQ ID NO 9)
                                          HindIII 13.6 5'  CTGGGTCTGG AAGCCCAGAA GCTTGAGTAC TCACCTGTAG CCATTGCCGC TAGG    (SEQ ID NO 10)
                             HindIII 13.7 5'  TTTTCTCGAG CTCCGCGCCT GGCCGGGGTC CCTC                         (SEQ ID NO 11)
             XhoI
```

The boldface regions of oligos 13.5 and 13.6 denote hGH sequences. The italicized regions correspond to the first 10 base pairs of hEPO intron 1. The remainder of the oligos correspond to hEPO sequences from −620 to −597 relative to the hEPO coding region. The non-boldface region of oligo 13.7 is identical to bases −1 to −24 relative to the hEPO coding region. The boldface region includes an XhoI site tail to convert the 3' boundary of the amplified fragment to an XhoI site.

Plasmid pXEPO-10 can be used for gene targeting by digestion with BamHI and XhoI to release the 7.3 kb fragment containing the mMT-I/hGH fusion flanked on both sides by hEPO sequences. This fragment (targeting fragment 1) contains no hEPO coding sequences, having only sequences lying between −620 and approximately '6620 upstream of the hEPO coding region and hEPO intron 1 sequences to direct targeting to the human EPO locus. targeting fragment 1 is transfected into primary or secondary human skin fibroblasts using conditions similar to those described in Example 1c. G418-resistant colonies are picked into individual wells of 96-well plates and screened for EPO expression by an ELISA assay (R&D Systems, Minneapolis Minn.). Cells in which the transfecting DNA integrates randomly into the human genome cannot produce EPO. Cells in which the transfecting DNA has undergone homologous recombination with the endogenous hEPO intron 1 and hEPO upstream sequences contain a chimeric gene in which the MMT-I promoter and non-transcribed sequences and the hGH 5' untranslated sequences and hGH exon 1 replace the normal hEPO promoter and hEPO exon 1 (see FIG. 5).

ing DNA has undergone homologous recombination with the endogenous hEPO promoter and upstream sequences contain a chimeric gene in which the mMT-I promoter and non-transcribed sequences, hGH 5' untranslated sequences and hGh exon 1, and a 10 base pair linker comprised of the first 10 bases of hEPO intron 1 are inserted at the HindIII site lying at position −620 relative to the hEPO coding region (see FIG. 6). The localization of the mMT-I promoter upstream of the normally silent hEPO promoter will direct the synthesis, in primary or secondary skin fibroblasts, of a message reading (5' to 3') non-translated metallothionein and hGH sequences, hGH exon 1, 10 bases of DNA identical to the first 10 base pairs of hEPO intron 1, and the normal hEPO promoter and hEPO exon 1 (−620 to +13 relative to the EPO coding sequence). The 10 base pair linker sequence from hEPO intron 1 acts as a splice donor site to fuse hGH exon 1 to the next downstream splice acceptor site, that lying immediately upstream of hEPO exon 2. Processing of the resulting transcript will therefore splice out the hEPO promoter, exon 1, and intron 1 sequences. The replacement of hEPO exon 1 with hGH exon 1 results in a protein in which the first 4 amino acids of the hEPO signal peptide are replaced with amino acids 1–3 of hGH, creating a functional, chimeric signal peptide which is removed by post-translation processing from the mature protein and is secreted from the expressing cells.

A series of constructs related to pXEPO-10 and PXEPO-11 can be constructed, using known methods. In these constructs, the relative positions of the mMT-I promoter and hGH sequences, as well as the position at which the mMT-I/hGH sequences are inserted into hEPO upstream sequences, are varied to create alternative chimeric transcription units that facilitate gene targeting, result in more efficient expression of the fusion transcripts, or have other desirable properties. Such constructs will give similar results, such that an hGH-hEPO fusion gene is placed under the control of an exogenous promoter by gene targeting to the normal hEPO locus. For example, the 6 kb HindIII-BamHI fragment upstream of the hEPO gene (See Example 1f) has numerous restriction enzyme recognition sequences that can be utilized as sites for insertion of the neo gene and the mMT-I promoter/hGH fusion fragment. One such site, a BglII site lying approximately 1.3 kb upstream of the HindIII site, is unique in this region and can be used for insertion of one or more selectable markers and a regulatory region derived from another gene that will serve to activate EPO expression in primary, secondary, or immortalized human cells.

First, the intermediate plasmid pT164 is constructed by inserting the 6 kb HindIII-BamHI fragment (Example 1f) lying upstream of the hEPO coding region into HindIII-BamHI digested pBluescriptII SK+ (Stratagene, LaJola, Calif.). Plasmid pMC1neoPolyA (Thomas, K. R. and Capecchi, M. R. Cell 51:503–512 (1987); available from Stratagene, LaJola, Calif. is digested with BamHI and XhoI, made blunt-ended by treatment with the Klenow fragment of E. coli DNA polymerase, and the resulting 1.1 kb fragment is purified. pT164 is digested with BglII and made blunt-ended by treatment with the Klenow fragment of E. coli DNA polymerase. The two preceding blunt-ended fragments are ligated together and transformed into competent E. coli. Clones with a single insert of the 1.1 kb neo fragment are isolated and analyzed by restriction enzyme analysis to identify those in which the BglII site recreated by the fusion of the blunt XhoI and BglII sites is localized 1.3 kb away from the unique HindIII site present in plasmid pT164. The resulting plasmid, pT165, can now be cleaved at the unique BglII site flanking the 5' side of the neo transcription unit.

Oligonucleotides 13.8 and 13.9 are utilized in polymerase chain reactions to generate a fragment in which the mouse metallothionein I (mMT-I) promoter—hGH exon 1 sequences are additionally fused to a 10 base pair fragment comprising a splice donor site. The splice donor site chosen corresponds to the natural hEPO intron 1 splice donor site, although a larger number of splice donor sites or consensus splice donor sites can be used. The oligonucleotides (13.8 and 13.9) are used to amplify the approximately 0.73 kb mMT-I promoter—hGH exon 1 fragment from pXGH5 (FIG. 1). The amplified fragment (fragment 7) is digested with BglII and ligated to BglII digested pT165. The ligation mixture is transformed into E. coli and a clone, containing a single insert of fragment 7 in which the KpnI site in the mMT-I promoter is adjacent to the 5' end of the neo gene and the mMT-I promoter is oriented such that transcription is directed towards the unique HindIII site, is identified and designated pXEPO-12.

```
13.8 5' AAAAAGATCT GGTACCTTGG TTTTTAAAAC CAGCCTGGAG    (SEQ ID NO 12)
         BglII    KpnI
```

The non-boldface region of oligo 13.8 is identical to the mMT-I promoter, with the natural KpnI site as its 5' boundary. The boldface type denotes a BglII site tail to convert the 5' boundary to a BglII site.

```
13.9 5' TTTTAGATCT GAGTACTCAC CTGTAGCCAT TGCCGCTAGG    (SEQ ID NO 13)
         BglII
```

The boldface region of oligos 13.9 denote hGH sequences. The italicized region corresponds to the first 10 base pairs of hEPO intron 1. The underlined BglII site is added for plasmid construction purposes.

Plasmid pXEPO-12 can be used for gene targeting by digestion with BamHI and HindIII to release the 7.9 kb fragment containing the neo gene and the mMT-I/hGH fusion flanked on both sided by hEPO sequences. This fragment (targeting fragment 3) contains no hEPO coding sequences, having only sequences lying between approximately −620 and approximately −6620 upstream of the hEPO coding region to direct targeting upstream of the human EPO locus. Targeting fragment 3 is transfected into primary, secondary, or immortalized human skin fibroblasts using conditions similar to those described in Examples 1b and 1c. G418-resistant colonies are picked into individual wells of 96-well plates and screened for EPO expression by an ELISA assay (R&D Systems, Minneapolis Minn). Cells in which the transfecting DNA integrates randomly into the human genome cannot produce EPO. Cells in which the transfecting DNA has undergone homologous recombination with the endogenous hEPO promoter and upstream sequences contain a chimeric gene in which the mMT-I promoter and non-transcribed sequences, hGH 5' untranslated sequences, and hGH exon 1, and a 10 base pair linker comprised of the first 10 bases of hEPO intron 1 are inserted at the BglII site lying at position approximately −1920 relative to the hEPO coding region. The localization of the mMT-I promoter upstream of the normally silent hEPO promoter will direct the synthesis, in primary, secondary, or immortalized human fibroblasts (or other human cells), of a message reading: (5' to 3') nontranslated metallothio-nein and hGH sequences, hGH exon 1, 10 bases of DNA identical to the first 10 base pairs of hEPO intron 1, and hEPO upstream region and hEPO exon 1 (from approximately −1920 to +13 relative to the EPO coding sequence). The 10 base pair linker sequence from hEPO intron 1 acts as a splice donor site to fuse hGH exon 1 to a downstream splice acceptor site, that lying immediately upstream of hEPO exon 2. Processing of the resulting transcript will therefore splice out the hEPO upstream sequences, promoter region, exon 1, and intron 1 sequences. When using pXEPO-10, -11 and -12, post-transcriptional processing of the message can be improved by using in vitro mutagenesis to eliminate splice acceptor sites lying in hEPO upstream sequences between the mMT-I promoter and hEPO exon 1, which reduce level of productive splicing events needed create the desired message. The replacement of hEPO exon 1 with hGH exon 1 results in a protein in which the first 4 amino acids of the hEPO signal peptide are replaced with amino acids 1–3 of hGH, creating a functional, chimeric signal peptide which is removed by post-translation processing from the mature protein and is secreted from the expressing cells.

Example 3

Targeted Modification of Sequences Upstream and Amplification of the Targeted Gene Human cells in which the EPO gene has been activated by the methods previously described (in copending U.S. patent applications Ser. Nos. 07/787,840 and 07/911,533) can be induced to amplify the neo/mMT-1 /EPO transcription unit if the targeting plasmid contains a marker gene that can confer resistance to a high level of a cytotoxic agent by the phenomenon of gene amplification. Selectable marker genes such as dihydrofolate reductase (dhfr, selective agent is methotrexate), the multifunctional CAD gene [encoding carbamyl phosphate synthase, aspartate transcarbamylase, and dihydro-orotase; selective agent is N-(phosphonoacetyl)-L-aspartate (PALA)], and adenosine deaminase (ada; selective agent is an adenine nucleoside), have been documented, among other genes, to be amplifiable in immortalized human cell lines (Wright, J. A. et al. Proc. Natl. Acad. Sci. USA 87:1791–1795 (1990)). In these studies, gene amplification has been documented to occur in a number of immortalized human cell lines. HT1080, HeLa, MCF-7 breast cancer cells, K-562 leukemia cells, KB carcinoma cells, or 2780AD ovarian carcinoma cells all display amplification under appropriate selection conditions.

Plasmids pXEPO-10 and pXEPO-11 can be modified by the insertion of a normal or mutant dhfr gene into the unique HindIII sites of these plasmids. After transfection of HT1080 cells with the appropriate DNA, selection for G418-resistance (conferred by the neo gene), and identification of cells in which the hEPO gene has been activated by gene targeting of the neo, dhfr, and mMT-1 sequences to the correct position upstream of the hEPO gene, these cells can be exposed to stepwise selection in methotrexate (MTX) in order to select for amplification of dhfr and co-amplification of the linked neo, mMT-1, and hEPO sequences (Kaufman, R. J. Technique 2:221–236 (1990)). A stepwise selection scheme in which cells are first exposed to low levels of MTX (0.01 to 0.08 $\mu$M), followed by successive exposure to incremental increases in MTX concentrations up to 250 $\mu$M MTX or higher is employed. Linear incremental steps of 0.04 to 0.08 $\mu$M MTX and successive 2-fold increases in MTX concentration will be effective in selecting for amplified transfected cell lines, although a variety of relatively shallow increments will also be effective. Amplification is monitored by increases in dhfr gene copy number and confirmed by measuring in vitro hEPO expression. By this strategy, substantial overexpression of hEPO can be attained by targeted modification of sequences lying completely outside of the hEPO coding region.

Constructs similar to those described (Examples 1i and 1k) to activate hGH expression in human cells can also be further modified to include the dhfr gene for the purpose of obtaining cells that overexpress the hGH gene by gene targeting to non-coding sequences and subsequent amplification.

Example 4

Figure 3:
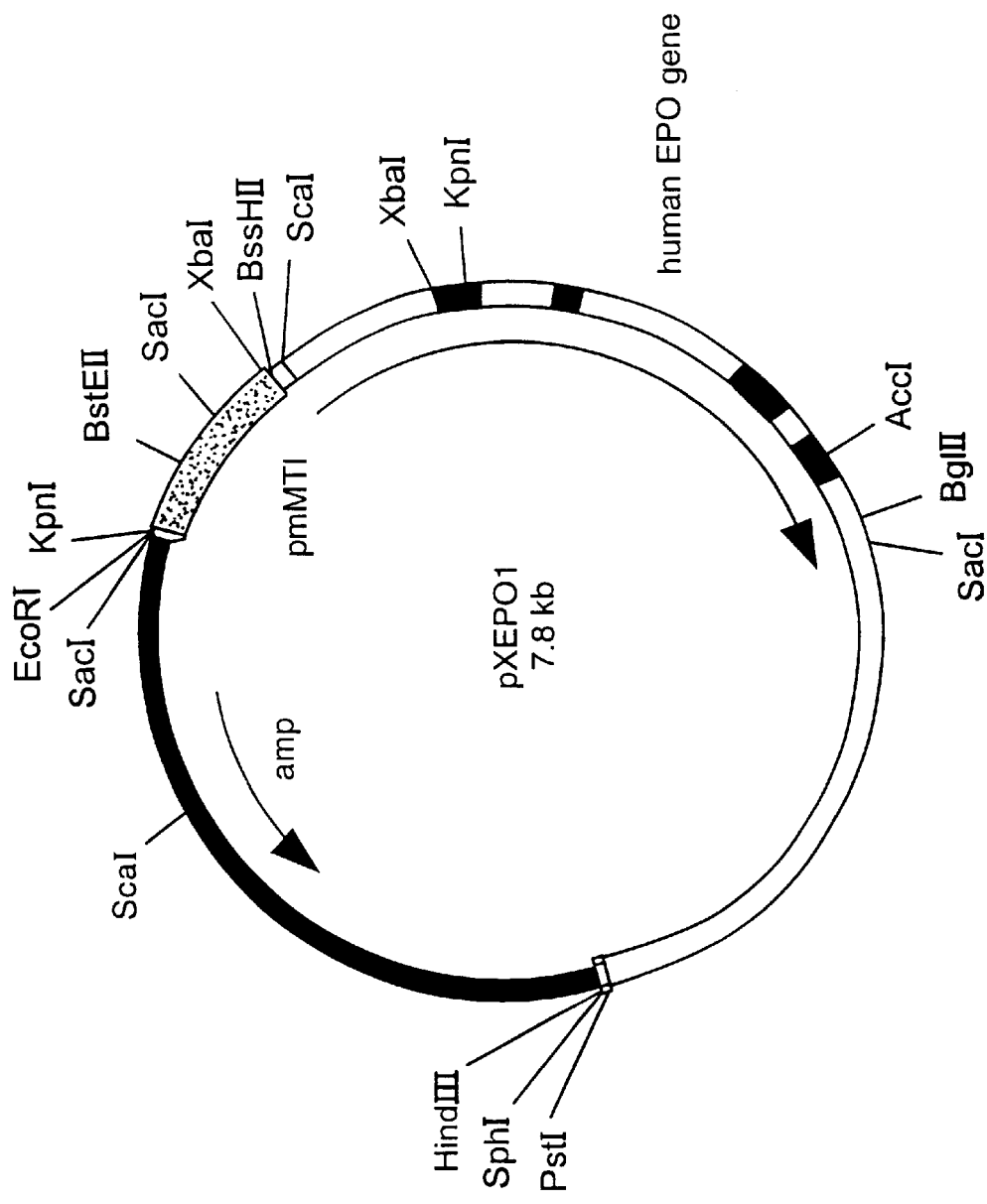
FIG. 3 is a schematic representation of plasmid pXEP01. The solid black arc represents the pUC12 backbone and the arrow denotes the direction of transcription of the ampicillin resistance gene. The stippled arc represents the mouse metallothionein promoter (pmMT1). The unfilled arc interrupted by black boxes represents the human erythropoietin EPO gene (the black boxes denote exons and the arrow indicates the direction hEPO transcription). The relative positions of restriction endonuclease recognition sites are indicated.

Targeting and Activation of the Human EPO Locus in an Immortalized Human Fibroblast Line The targeting construct pXEPO-13 was made to test the hypothesis that the endogenous hEPO gene could be activated in a human fibroblast cell. First, plasmid pT22.1 was constructed, containing 63 bp of genomic hEPO sequence upstream of the first codon of the hEPO gene fused to the mouse metallothionein-1 promoter (mMT-I). Oligonucleotides 22.1 to 22.4 were used in PCR to fuse mMT-I and hEPO sequences. The properties of these primers are as follows: 22.1 is a 21 base oligonucleotide homologous to a segment of the mMT-I promoter beginning 28 bp upstream of the mMT-I KpnI site; 22.2 and 22.3 are 58 nucleotide complementary primers which define the fusion of hEPO and mMT-I sequences such that the fusion contains 28 bp of hEPO sequence beginning 35 bases upstream of the first codon of the hEPO gene, and mMT-I sequences beginning at base 29 of oligonucleotide 22.2, comprising the natural BglII site of mMT-I and extending 30 bases into mMT-I sequence; 22.4 is 21 nucleotides in length and is homologous to hEPO sequences beginning 725 bp downstream of the first codon of the hEPO gene. These primers were used to amplify a 1.4 kb DNA fragment comprising a fusion of mMT-I and hEPO sequences as described above. The resulting fragment was digested with KpnI (the PCR fragment contained two KpnI sites: a single natural KpnI site in the mMT-I promoter region and a single natural KpnI site in the hEPO sequence), and purified. The plasmid pXEPO1 (FIG. 3) was also digested with KpnI, releasing a 1.4 kb fragment and a 6.4 kb fragment. The 6.4 kb fragment was purified and ligated to the 1.4 kb KpnI PCR fusion fragment. The resulting construct was called pT22.1. A second intermediate, pT22.2, was constructed by ligating the approximately 6 kb HindIII-BamHI fragment lying upstream of the hEPO structural gene (see Example 1f) to BamHI and HindIII digested pBSIISK+ (Stratagene, LaJola, Calif.). A third intermediate, pT22.3, was constructed by first excising a 1.1 kb XhoI/BamHI fragment from pMCI-NEOpolyA (Stratagene., LaJola, Calif.) containing the neomycin phosphotransferase gene. The fragment was then made blunt-ended with the Klenow fragment of DNA polymerase I (New England Biolabs). This fragment was then ligated to the HincII site of pBSIISK+ (similarly made blunt with DNA polymerase I) to produce pT22.3. A fourth intermediate, pT22.4, was made by purifying a 1.1 kb XhoI/HindIII fragment comprising the neo gene from pT22.3 and ligating this fragment to XhoI and HindIII digested pT22.2. pT22.4 thus contains the neo gene adjacent to the HindIII side of the BamHI-HindIII upstream hEPO fragment. Finally, pXEPO-13 was generated by first excising a 2.0 kb EcoRI/AccI fragment from pT22.1. The EcoRI site of this fragment defines the 5' boundary of the mMT-I promoter, while the AccI site of this fragment lies within hEPO exon 5. Thus, the AccI/EcoRI fragment contains a nearly complete hEPO expression unit, missing only a part of exon 5 and the natural polyadenylation site. This 2.0 kb EcoRI/AccI fragment was purified, made blunt-ended by treatment with the Klenow fragment of DNA polymerase I, and ligated to XhoI digested, blunt-ended, pT22.4.

HT1080 cells were transfected with PvuI-BamHI digested pXEPO-13. pXEPO-13 digested in this way generates three fragments; a 1 kb vector fragment including a portion of the amp gene, a 1.7 kb fragment of remaining vector sequences and an approximately 10 kb fragment containing hEPO, neo and mMT-I sequences. This approximately 10 kb BamHI/PvuI fragment contained the following sequences in order from the BamHI site: an approximately 6.0 kb of upstream hEPO genomic sequence, the 1.1 kb neo transcription unit, the 0.7 kb mMT-I promoter and the 2.0 kb fragment containing hEPO coding sequence truncated within exon 5. 45μg of pEXPO-13 digested in this way was used in an electroporation of 12 million cells (electroporation conditions were described in Example 1b). This electroporation was repeated a total of eight times, resulting in electroporation of a total of 96 million cells. Cells were mixed with media to provide a cell density of 1 million cells per ml and 1 ml aliquots were dispensed into a total of 96, 150 mm tissue culture plates (Falcon) each containing a minimum of 35 ml of DMEM/15% calf serum. The following day, the media was aspirated and replaced with fresh medium containing 0.8 mg/ml G418 (Gibco). After 10 days of incubation, the media of each plate was sampled for hEPO by ELISA analysis (R & D Systems). Six of the 96 plates contained at least 10 mU/ml hEPO. One of these plates, number 18, was selected for purification of hEPO expressing colonies. each of the 96, 150 mm plates contained approximately 600 G418 resistant colonies (an estimated total of 57,600 G418 resistant colonies on all 96 plates). The approximately 600 colonies on plate number 18 were trypsinized and replated at 50 cells/ml into 364 well plates (Sterilin). After one week of incubation, single colonies were visible at approximately 10 colonies per large well of the 364 well plates (these plates are comprised of 16 small wells within each of the 24 large wells). Each well was screened for hEPO expression at this time. Two of the large wells contained media with at least 20 mU/ml hEPO. Well number A2 was found to contain 15 colonies distributed among the 16 small wells. The contents of each of these small wells were trypsinized and transferred to 16 individual wells of a 96 well plate following 7 days of incubation the media from each of these wells was sampled for hEPO ELISA analysis. Only a single well, well number 10, contained hEPO. This cell strain was designated HT165-18A2-10 and was expanded in culture for quantitative hEPO analysis, RNA isolation and DNA isolation. Quantitative measurement of hEPO production resulted in a value of 2,500 milliunits/million cells/24 hours.

A 0.2 kb DNA probe extending from the AccI site in hEPO exon 5 to the BglII site in the 3' untranslated region was used to probe RNA isolated from HT165-18A2-10 cells. The targeting construct, pXEPO-13, truncated at the AccI site in exon 5 does not contain these AccI/BglII sequences and, therefore, is diagnostic for targeting at the hEPO locus. Only cell strains that have recombined in a homologous manner with natural hEPO sequences would produce an hEPO mRNA containing sequence homologous to the AccI/BglII sequences. HT165-18A2-10 was found to express an mRNA of the predicted size hybridizing with the 32-P labeled AccI/BglII hEPO probe on Northern blots. Restriction enzyme and Southern blot analysis confirmed that the neo gene and mMT-I promoter were targeted to one of the two hEPO alleles in HT165-18A2-10 cells.

These results demonstrate that homologous recombination can be used to target a regulatory region to a gene that is normally silent in human fibroblasts, resulting in the functional activation of that gene.

```
22.1 5' CACCTAAAAT GATCTCTCTG G                                                    (SEQ ID NO 14)

22.2 5' CGCGCCGGGT GACCACACCG GGGGCCCTAG ATCTGGTGAA GCTGGAGCTA CGGAGTAA            (SEQ ID NO 15)

22.3 5' TTACTCCGTA GCTCCAGCTT CACCAGATCT AGGGCCCCCG GTGTGGTCAC CCGGCGCG            (SEQ ID NO 16)

22.4 5' GTCTCACCGT GATATTCTCG G                                                    (SEQ ID NO 17)
```

EXAMPLE 5

Production of Intronless Genes

Gene targeting can also be used to produce a processed gene, devoid of introns, for transfer into yeast or bacteria for gene expression and in vitro protein production. For example, hGH can by produced in yeast by the approach described below.

Two separate targeting constructs are generated. Targeting construct 1 (TC1) includes a retroviral LTR sequence, for example the LTR from the Moloney Murine Leukemia Virus (MoMLV), a marker for selection in human cells (e.g., the neo gene from Tn5), a marker for selection in yeast (e.g., the yeast URA3 gene), a regulatory region capable of directing gene expression in yeast (e.g., the GAL4 promoter), and optionally, a sequence that, when fused to the hGH gene, will allow secretion of hGH from yeast cells (leader sequence). The vector can also include a DNA sequence that permits retroviral packaging in human cells. The construct is organized such that the above sequences are flanked, on both sides, by hGH genomic sequences which, upon homologous recombination with genomic hGH gene N sequences, will integrate the exogenous sequences in TC1 immediately upstream of hGH gene N codon 1 (corresponding to amino acid position 1 in the mature, processed protein). The order of DNA sequences upon integration is: hGH upstream and regulatory sequences, neo gene, LTR, URA3 gene, GAL4 promoter, yeast leader sequence, hGH sequences including and downstream of amino acid 1 of the mature protein. Targeting Construct 2 (TC2) includes sequences sufficient for plasmid replication in yeast (e.g., 2-micron circle or ARS sequences), a yeast transcriptional termination sequence, a viral LTR, and a marker gene for selection in human cells (e.g., the bacterial gpt gene). The construct is organized such that the above sequences are flanked on both sides by hGH genomic sequences which, upon homologous recombination with genomic hGH gene N sequences, will integrate the exogenous sequences in TC2 immediately downstream of the hGH gene N stop codon. The order of DNA sequences upon integration is: hGH exon 5 sequences, yeast transcription termination sequences, yeast plasmid replication sequences, LTR, gpt gene, hGH 3' non-translated sequences.

Linear fragments derived from TC1 and TC2 are sequentially targeted to their respective positions flanking the hGH gene. After superinfection of these cells with helper retrovirus, LTR directed transcription through this region will result in an RNA with LTR sequences on both ends.

Splicing of this RNA will generate a molecule in which the normal hGH introns are removed. Reverse transcription of the processed transcript will result in the accumulation of double-stranded DNA copies of the processed hGH fusion gene. DNA is isolated from the doubly-targeted, retrovirally-infected cells, and digested with an enzyme that cleaves the transcription unit once within the LTR. The digested material is ligated under conditions that promote circularization, introduced into yeast cells, and the cells are subsequently exposed to selection for the URA3 gene only cells which have taken up the URA3 gene (linked to the sequences introduced by TC1 and TC2 and the processed hGH gene) can grow. These cells contain a plasmid which will express the hGH protein upon galactose induction and secrete the hGH protein from cells by virtue of the fused yeast leader peptide sequence which is cleaved away upon secretion to produce the mature, biologically active, hGH molecule.

Expression in bacterial cells is accomplished by simply replacing, in TC1 and TC2, the ampicillin-resistance gene from pBR322 for the yeast URA3 gene, the tac promoter (deBoer et al., *Proc. Natl. Acad. Sci.* 80:21–25 (1983)) for the yeast GAL4 promoter, a bacterial leader sequence for the yeast leader sequence, the pBR322 origin of replication for the 2-micron circle or ARS sequence, and a bacterial transcriptional termination (e.g., trpA transcription terminator; Christie, G. E. et al., *Proc. Natl. Acad. Sci,* 78:4180–4184 (1981)) sequence for the yeast transcriptional termination sequence. Similarly, hEPO can be expressed in yeast and bacteria by simple replacing the hGH targeting sequences with hEPO targeting sequences, such that the yeast or bacterial leader sequence is positioned immediately upstream of hEPO codon 1 (corresponding to amino acid position 1 in the mature processed protein).

Equivalents

Those skilled in the art will recognize, or be able to ascertain using not more than routine experimentation, many equivalents to the specific embodiments of the invention described herein. Such equivalents are intended to be encompassed by the following claims.

---

What is claimed is:

1. A method of altering the expression of a targeted gene in a cell, the method comprising the steps of:
    (a) providing a DNA construct comprising:
        (i) a targeting sequence;
        (ii) an exogenous regulatory sequence;
        (iii) an exon; and
        (iv) an unpaired splice-donor site at the 3' end of the exon,
    (b) providing a cell, the genome of which comprises
        (i) a target site homologous to the targeting sequence, and;
        (ii) a targeted gene having an endogenous regulatory region;
    c) transfecting the cell with the DNA construct in vitro, thereby producing a transfected cell;
    d) maintaining the transfected cell under conditions appropriate for homologous recombination, thereby producing a homologously recombinant cell, the genome of which comprises the exogenous regulatory sequence, the construct-derived exon, and the construct-derived splice-donor site, in addition to all endogenous exons of the targeted gene; and
    e) maintaining the homologously recombinant cell under conditions appropriate for transcription under the control of the exogenous regulatory sequence, to produce a transcript of the construct-derived exon, the targeted gene, and any sequence lying between the construct-derived exon and the targeted gene, wherein the RNA of the transcript corresponding to the construct-derived splice-donor site directs splicing to a splice-acceptor site in the transcript which corresponds to a site within the targeted gene.

2. The method of claim 1 further comprising the steps of:
(f) maintaining the homologously recombinant cell under conditions appropriate for splicing and translation of the transcript; and
(g) confirming that a translation product of the spliced transcript was produced.

3. A cultured vertebrate cell into the genome of which is incorporated transcription unit, wherein the transcription unit comprises an exogenous regulatory sequence, an exogenous exon, and a splice-donor site at the 3' end of the exogenous exon, all located upstream of the endogenous transcription initiation site of an endogenous gene, the splice-donor site being operatively linked to the endogenous splice-acceptor site of the second endogenous exon of the endogenous gene.

4. The cultured vertebrate cell of claim 3, wherein the cell is selected from the group consisting of: HT1080 cells, HeLa cells, MCF-7 breast cancer cells, K-562 leukemia cells, KB carcinoma cells, 2780AD ovarian carcinoma cells, chinese hamster ovary (CHO) cells, and mouse L cells.

5. A cultured cell having incorporated therein a new transcription unit, wherein the new transcription unit comprises an exogenous inducible promoter operatively linked to an endogenous gene in the chromosomal DNA of the cell, provided that the exogenous inducible promoter is not identical to the endogenous promoter of the endogenous gene, and wherein the cell is selected from the group consisting of HT1080 cells, MCF-7 breast cancer cells, K-562 leukemia cells, KB carcinoma cells, 2780AD ovarian carcinoma cells, Chinese hamster ovary (CHO) cells, and mouse L cells.

6. A method of providing a protein to a mammal, comprising introducing into the mammal a homologoudsly recombinant cell which produces the protein, the homologously recombinant cell being generated by an in vitro process comprising:
(a) providing a DNA construct comprising:
  (1) a targeting sequence,
  (2) an exogenous regulatory sequence,
  (3) an exon, and
  (4) an unpaired splice-donor site at the 3' end of the exon
(b) providing a vertebrate cell, the genome of which comprises;
  (i) a target site homologous to the targeting sequence, and
  (ii) a targeted endogenous gene having an endogenous regulatory region;
(c) transfecting the vertebrate cell with the DNA construct, thereby producing a transfected cell;
(d) maintaining the transfected cell under conditions appropriate for homologous recombination, thereby producing a homologously recombinant cell the genome of which comprises the exogenous regulatory sequence, the construct-derived exon, and the construct-derived splice-donor site, in addition to all endogenous exons of the targeted gene; and
(e) maintaining the homologously recombinant cell under conditions appropriate for transcription under the control of the exogenous regulatory sequence, to produce a transcript of the construct-derived exon, the targeted gene, and any sequence lying between the construct-derived exon and the targeted gene, wherein the RNA of the transcript corresponding to the construct-derived splice-donor site directs splicing to a splice-acceptor site in the transcript which corresponds to a site within the targeted gene.

7. The method of claim 6, wherein the homologously recombinant cell is, prior to introduction into the mammal, enclosed within a barrier device which permits passage of the protein from the interior of the barrier device to the exterior of the barrier device.

8. A DNA construct that alters the expression of a targeted gene in a cell when the DNA construct is homologously recombined with a target site within the chromosomal DNA of the cell, the DNA construct comprising:
(a) a targeting sequence homologous to the target site;
(b) an exogenous regulatory sequence;
(c) an exon; and
(d) an unpaired splice-donor site at the 3' end of the exon;
  wherein, following homologous recombination of the targeting sequence with the target site, the chromosomal DNA of the cell comprises the construct-derived exon in addition to all endogenous exons of the targeted gene, and wherein the targeted gene encodes a hormone, a cytokine, an antigen, an antibody, an enzyme, a clotting factor, a transport protein, a receptor, a regulatory protein, a structural protein, or a transcription factor.

9. A DNA construct that alters the expression of a targeted gene in a cell when the DNA construct is homologously recombined with a target site within the chromosomal DNA of the cell, the DNA construct comprising:
(a) a targeting sequence homologous to the target site;
(b) an exogenous regulatory sequence;
(c) an exon; and
(d) an unpaired splice-donor site at the 3' end of the exon;
  wherein, following homologous recombination of the targeting sequence with the target site, the chromosomal DNA of the cell comprises the construct-derived exon in addition to all endogenous exons of the targeted gene, and wherein the targeted gene encodes a protein selected from the group consisting of calcitonin, insulin, insulinotropin, insulin-like growth factors, parathyroid hormone, nerve growth factors, interleukins, immunoglobulins, catalytic antibodies, superoxide dismutase, tissue plasminogen activators, blood clotting factor VIII, apolipoprotein E, apolipoprotein A-I, globins, low density lipoprotein receptor, IL2 receptor, IL-2 receptor antagonists, alpha-1 antitrypsin, immune response modifiers, growth hormone, interferon, blood clotting factor IX, glucocerebrosidase, a colony stimulating factor, and erythropoietuin..

10. A DNA construct that alters the expression of a targeted gene in a cell when the DNA construct is homologously recombined with a target site within the chromosomal DNA of the cell, the DNA construct comprising:
(a) a targeting sequence homologous to the target site;
(b) an exogenous regulatory sequence;
(c) an exon; and
(d) an unpaired splice-donor site at the 3' end of the exon;
  wherein, following homologous recombination of the targeting sequence with the target site, the chromosomal DNA of the cell comprises the construct-derived exon in addition to all endogenous exons of the targeted gene, and wherein the exogenous regulatory sequence is a promoter, an enhancer, a scaffold-attachment region, a negative regulatory element, a transcriptional initiation site, or a regulatory protein binding site.

11. A DNA construct that alters the expression of a targeted gene in a cell when the DNA construct is homologously recombined with a target site within the chromosomal DNA of the cell, the DNA construct comprising:

(a) a targeting sequence homologous to the target site;
(b) an exogenous regulatory sequence;
(c) an exon;
(d) an unpaired splice-donor site at the 3' end of the exon; and
(e) an amplifiable marker gene;

wherein, following homologous recombination of the targeting sequence with the target site, the chromosomal DNA of the cell comprises the construct-derived exon in addition to all endogenous exons of the targeted gene.

* * * * *